US006228817B1

(12) United States Patent
Coolbaugh et al.

(10) Patent No.: US 6,228,817 B1
(45) Date of Patent: *May 8, 2001

(54) DISPERSANTS AND DISPERSANT VISCOSITY INDEX IMPROVERS FROM SELECTIVELY HYDROGENATED POLYMERS

(75) Inventors: Thomas S. Coolbaugh, Yardley, PA (US); John E. Marlin, II, Bridgewater, NJ (US); Demetrios N. Matthews, Edison, NJ (US); Kenneth G. Stensler, Somerset, NJ (US); Frederick C. Loveless, Middlebury, CT (US)

(73) Assignee: Mobil Oil Corporation, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/102,681

(22) Filed: Jun. 23, 1998

Related U.S. Application Data

(63) Continuation-in-part of application No. 08/734,982, filed on Oct. 22, 1996, now Pat. No. 5,780,540, which is a continuation-in-part of application No. 08/488,046, filed on Jun. 7, 1995, now Pat. No. 5,633,415, and a continuation-in-part of application No. 08/476,016, filed on Jan. 7, 1995, now Pat. No. 5,637,783, which is a continuation-in-part of application No. 08/382,814, filed on Feb. 3, 1995, now Pat. No. 5,545,783, which is a division of application No. 08/179,051, filed on Jan. 7, 1994, now Pat. No. 5,387,730, which is a division of application No. 07/992,341, filed on Dec. 17, 1992, now Pat. No. 5,288,937, which is a continuation of application No. 07/907,959, filed on Aug. 6, 1992, now Pat. No. 5,210,359, which is a division of application No. 07/466,135, filed on Jan. 16, 1990, now Pat. No. 5,149,895.

(51) Int. Cl.[7] ............................................. C10M 145/80
(52) U.S. Cl. ........................ 508/185; 508/189; 525/327.7; 525/337; 525/338
(58) Field of Search ............................ 508/185, 189; 525/327.7, 338, 337

(56) References Cited

U.S. PATENT DOCUMENTS

| | | | |
|---|---|---|---|
| 3,311,598 | 3/1967 | Mertzweiller et al. | 260/85.1 |
| 3,413,347 | 11/1968 | Worrel | 260/570.5 |
| 3,438,757 | 4/1969 | Honnen et al. | 44/58 |
| 3,442,808 | 5/1969 | Traise et al. | 252/49.6 |
| 3,539,633 | 11/1970 | Piasek et al. | 260/570.5 |
| 3,634,515 | 1/1972 | Pisaek et al. | 260/570.5 |
| 3,649,229 | 3/1972 | Otto | 44/73 |
| 3,697,574 | 10/1972 | Piasek et al. | 260/462 |
| 3,725,277 | 4/1973 | Worrel | 252/51.5 |
| 3,725,480 | 4/1973 | Traise et al. | 250/583 |
| 3,726,882 | 4/1973 | Traise et al. | 260/296 |
| 3,798,165 | 3/1974 | Piasek et al. | 252/51.5 |
| 4,092,255 | 5/1978 | Chapelet et al. | 252/50 |
| 4,146,489 | 3/1979 | Stambaugh et al. | 252/50 |
| 4,234,435 | 11/1980 | Melshardt | 252/51.5 |
| 4,454,059 | 6/1984 | Pindar et al. | 252/51.5 |
| 4,810,754 | 3/1989 | McCrary | 525/264 |
| 4,832,702 | 5/1989 | Kummer et al. | 44/62 |
| 5,102,566 | 4/1992 | Fetterman et al. | 252/32.7 |
| 5,128,086 | 7/1992 | Tomko et al. | 264/272.11 |
| 5,140,075 | 8/1992 | Tomko et al. | 525/286 |
| 5,149,895 | 9/1992 | Coobaugh et al. | 585/507 |
| 5,187,236 | 2/1993 | Coolbaugh et al. | 525/314 |
| 5,210,359 | 5/1993 | Coolbaugh et al. | 585/507 |
| 5,268,427 | 12/1993 | Coolbaugh et al. | 525/98 |
| 5,276,100 | 1/1994 | Coolbaugh et al. | 525/314 |
| 5,288,937 | 2/1994 | Coolbaugh et al. | 585/507 |
| 5,292,820 | 3/1994 | Coolbaugh et al. | 525/314 |
| 5,306,780 | 4/1994 | Coolbaugh et al. | 525/314 |
| 5,352,743 | 10/1994 | Coolbaugh et al. | 525/314 |
| 5,359,009 | 10/1994 | Coolbaugh et al. | 525/314 |
| 5,376,722 | 12/1994 | Coolbaugh et al. | 525/102 |
| 5,387,730 | 2/1995 | Coolbaugh et al. | 585/10 |
| 5,399,629 | 3/1995 | Coolbaugh et al. | 525/314 |
| 5,416,163 | 5/1995 | Coolbaugh et al. | 525/98 |
| 5,438,102 | 8/1995 | Brandes et al. | 525/314 |
| 5,457,161 | 10/1995 | Coolbaugh et al. | 525/314 |
| 5,464,549 | 11/1995 | Sieberth | 252/51.5 |
| 5,470,914 | 11/1995 | Coolbaugh et al. | 525/66 |
| 5,510,548 | 4/1996 | Coolbaugh et al. | 525/12 |
| 5,530,068 | 6/1996 | Coolbaugh et al. | 525/314 |
| 5,545,783 | 8/1996 | Coolbaugh et al. | 585/12 |
| 5,552,492 | 9/1996 | Brandes et al. | 525/314 |
| 5,569,718 | 10/1996 | Coolbaugh et al. | 525/314 |
| 5,585,441 | 12/1996 | Brandes et al. | 525/193 |
| 5,625,100 | 4/1997 | Coolbaugh et al. | 585/12 |
| 5,633,415 | 5/1997 | Brandes et al. | 585/12 |
| 5,637,783 | 6/1997 | Brandes et al. | 585/12 |
| 5,663,126 | 9/1997 | Boden et al. | 508/221 |
| 5,663,130 | 9/1997 | Emert et al. | 508/506 |
| 5,663,239 | 9/1997 | Coolbaugh et al. | 525/314 |
| 5,691,422 | 11/1997 | Emert et al. | 525/338 |
| 5,717,035 | 2/1998 | Coolbaugh et al. | 525/314 |
| 5,747,598 | 5/1998 | Coolbaugh et al. | 525/314 |
| 5,767,046 | * 6/1998 | Cusumano et al. | 508/443 |
| 5,773,524 | 6/1998 | Coolbaugh et al. | 525/332.8 |
| 5,780,540 | 7/1998 | Brandes et al. | 524/572 |
| 5,804,667 | * 9/1998 | Diana et al. | 525/327.9 |
| 5,811,378 | * 9/1998 | Lange | 508/241 |
| 5,936,041 | * 8/1999 | Diana et al. | 525/327.6 |

* cited by examiner

*Primary Examiner*—Jacqueline V. Howard

(57) ABSTRACT

The invention provides dispersants and dispersant viscosity index improvers which include polymers of conjugated dienes which have been hydrogenated, functionalized, optionally modified, and post treated. The dispersant substances include a copolymer of two different conjugated dienes. The polymers are selectively hydrogenated to produce polymers which have highly controlled amounts of unsaturation, permitting highly selective functionalization. Also provided are lubricant fluids, such as mineral and synthetic oils, which have been modified in their dispersancy and/or viscometric properties by means of the dispersant substances of the invention. Also provided are methods of modifying the dispersancy and/or viscometric properties of lubricating fluids such as mineral and synthetic lubricating oils. The dispersant substances may also include a carrier fluid to provide dispersant concentrates.

35 Claims, No Drawings

DISPERSANTS AND DISPERSANT VISCOSITY INDEX IMPROVERS FROM SELECTIVELY HYDROGENATED POLYMERS

CROSS-REFERENCE TO RELATED APPLICATION

The application is a continuation in part of U.S. application Ser. No. 08/734,982, filed Oct. 22, 1996 now U.S. Pat. No. 5,780,540, which is a continuation in part of U.S. application Ser. No. 08/488,046, filed Jun. 7, 1995, and now U.S. Pat. No. 5,633,415; and U.S. application Ser. No. 08/476,016, filed Jan. 7, 1995, and now U.S. Pat. No. 5,637,783; both of which are a continuation in part of U.S. application Ser. No. 08/382,814, filed Feb. 3, 1995, and now U.S. Pat. No. 5,545,783, which is a divisional of U.S. application Ser. No. 08/179,051 filed Jan. 7, 1994, and now U.S. Pat. No. 5,387,730, which is a divisional of U.S. application Ser. No. 07/992,341, filed Dec. 17, 1992, and now U.S. Pat. No. 5,288,937, which is a continuation of U.S. application Ser. No. 07/907,959 filed Aug. 6, 1992, and now U.S. Pat. No. 5,210,359, which is a divisional of U.S. application Ser. No. 07/466,135 filed Jan. 16, 1990, and now U.S. Pat. No. 5,149,895. The entire contents of U.S. application Ser. No. 07/466,135 are incorporated herein by reference.

BACKGROUND OF THE INVENTION

This invention relates to dispersants, dispersants with improved engine performance, dispersants with viscosity index (VI) improving properties, and dispersant VI improvers from functionalized diene polymers, and methods of their use. More particularly, the invention relates to dispersants, dispersants with VI improving properties, and dispersant VI improvers from selectively hydrogenated copolymers prepared using conjugated dienes. The invention is additionally directed to dispersants, dispersants with VI improving properties, and dispersant VI improvers from chemically modified derivatives of the above polymers.

Liquid elastomers are well known and are used in various applications. For example, many functionally terminated polybutadiene liquid elastomers are known. These materials are generally highly unsaturated and frequently form the base polymer for polyurethane formulations. The preparation and application of hydroxy-terminated polybutadiene is detailed by J. C. Brosse et al. in *Hydroxyl-terminated polymers obtained by free radical polymerization—Synthesis, characterization and applications, Advances in Polymer Science* 81, Springer-Verlag, Berlin, Heidelberg, 1987, pp. 167 –220.

Also, liquid polymers possessing acrylate, carboxy- or mercapto-terminals are known. In addition to butadiene, it is known to utilize isoprene as the base monomer for the liquid elastomers. The liquid elastomers may contain additional monomers, such as styrene or acrylonitrile, for controlling compatibility in blends with polar materials, such as epoxy resins.

Also known in the prior art are pure hydrocarbon, non-functionalized liquid rubbers. These liquid elastomers contain varying degrees of unsaturation for utilization in vulcanization. Typical of highly unsaturated liquid elastomers is polybutadiene, e.g., that sold under the name RICON by Ricon Resins, Inc. A liquid polyisoprene which has been hydrogenated to saturate 90% of its original double bonds is marketed as LIR-290 by Kuraray Isoprene Chemical Co. Ltd. Still more highly saturated are liquid butyl rubbers available from Hardman Rubber Co., and Trilene, a liquid ethylene-propylene-diene rubber (EPDM) available from Uniroyal Chemical Co. The more highly saturated liquid elastomers exhibit good oxidation and ozone resistance properties.

Falk, *Journal of Polymer Science: PART A*-1, 9:2617–23 (1971), the entire contents of which are incorporated herein by reference, discloses a method of hydrogenating 1,4,-polybutadiene in the presence of 1,4-polyisoprene. More particularly, Falk discloses hydrogenation of the 1,4-polybutadiene block segment in the block copolymer of 1,4-polybutadiene-1,4-polyisoprene-1,4-polybutadiene and in random copolymers of butadiene and isoprene, with both polymerized monomers having predominantly 1,4-microstructure. Hydrogenation is conducted in the presence of hydrogen and a catalyst made by the reaction of organoaluminum or lithium compounds with transition metal salts of 2-ethylhexanoic acid. Falk, *Die Angewandte Chemie*, 21(286):17–23 (1972), the entire contents of which are also incorporated herein by reference, discloses the hydrogenation of 1,4-polybutadiene segments in a block copolymer of 1,4-polybutadiene-1,4-polyisoprene-1,4-polybutadiene.

Hoxmeier, Published European Patent application 88202449.0, filed on Nov. 2, 1988, Publication Number 0 315 280, published on May 10, 1989, discloses a method of selectively hydrogenating a polymer made from at least two different conjugated diolefins. One of the two diolefins is more substituted in the 2, 3 and/or 4 carbon atoms than the other diolefin and produces tri- or tetra-substituted double bond after polymerization. The selective hydrogenation is conducted under such conditions as to hydrogenate the ethylenic unsaturation incorporated into the polymer from the lesser substituted conjugated diolefin, while leaving unsaturated at least a portion of the tri- or tetra-substituted unsaturation incorporated into the polymer by the more substituted conjugated diolefin.

Mohajer et al., *Hydrogenated linear block copolymers of butadiene and isoprene: Effects of variation of composition and sequence architecture on properties, Polymer* 23:1523–35 (1982) discloses essentially completely hydrogenated butadiene-isoprene-butadiene(HBIB), HIBI and HBI block copolymers in which butadiene has predominantly 1,4-microstructure.

Kuraray K K, Japanese published patent application Number JP-328 729, filed on Dec. 12, 1987, published on Jul. 4, 1989, discloses a resin composition comprising 70–99% wt. of a polyolefin (preferably polyethylene or polypropylene) and 1–30% wt. of a copolymer obtained by hydrogenation of at least 50% of unsaturated bond of isoprene/butadiene copolymer.

Ashless dispersants are additives to lubricant fluids such as fuels and lubricating oils which improve the dispersability of the fluids or improve their viscometric properties. Typically, such dispersants are modified polymers, having an oleophilic polymer backbone to assure good solubility and to maintain particles suspended in the oil, and polar functionality to bind or attach to oxidation products and sludge. Dispersants generally have a solubilizing oleophilic (hydrophobic) tail and a polar (hydrophilic) head, forming micelles when actively bound to sludge.

Common dispersants include polyisobutenes which have been modified by the ene reaction to include functional groups such as succinimides, hydroxyethyl imides, succinate esters/amides, and oxazolines. Other dispersants include Mannich base derivatives of polybutenes, ethylene propylene polymers, and acrylic polymers.

Traditionally, dispersants have been polybutenes functionalized at one site in the molecule via an ene reaction with maleic anhydride followed by imidization with a polyamine. The polybutenes are typically 500–2,000 in molecular weight, and due to the polymerization process employed in their manufacture, have no more than one double bond per polybutene molecule. Accordingly, the number of potential functional groups per chain is limited to about one. Typically, this site is at a terminal portion of the molecule. Moreover, it is generally accepted that, in order to obtain beneficial dispersant properties, a molecule must have at least one functional group per approximately 2,000 molecular weight. Consequently, the molecular weight of traditional polybutene dispersants cannot exceed 2,000 if the desired functionality/hydrocarbon ratio is to be maintained. In addition, traditional dispersants have had molecular structures which have limited the placement of functional groups, generally requiring that such groups be placed at the terminal regions of the molecules.

The polymerization process for the traditional butene polymers has also generated products having an unacceptably wide distribution of molecular weights, i.e., an unacceptably high ratio of weight average molecular weight ($M_w$) to number average molecular weight ($M_n$). Typically, such distributions are $M_w/M_n \geq 2.5$, producing compositions whose dispersant properties are not well defined.

Moreover, functionalization reactions in these polymers have typically yielded substantial quantities of undesirable by-products such as insoluble modified polymers of variant molecular weight. Functionalization reactions can also result in compounds which contain undesirable chemical moieties such as chlorine.

U.S. Pat. No. 4,007,121 to Holder et al. describes lubricant additives which include polymers such as ethylene propylene polymers (EPT) having N-hydrocarbylcarboxamide groups.

U.S. Pat. Nos. 3,868,330 and 4,234,435 to Meinhardt et al. disclose carboxylic acid acylating agents for modification of lubricant additives. Modified polyalkenes are described such as polyisobutene-substituted succinic acylating agents having $M_n$ of 1300–5000 and $M_w/M_n$ of 1.5–4. These processes employ chlorination to provide greater functionality.

Heretofore, the art has failed to produce dispersants and dispersant VI improvers having selective and controllable amounts of polar functionality in their polymeric structure. Thus, the art has failed to provide any means of developing dispersants and dispersant VI improvers having higher molecular weights and/or higher amounts of functionalization per molecule. The art has also failed to provide dispersant polymers having desirably narrow molecular weight distributions to avoid the presence of by-products which degrade dispersant performance. The art has also failed to provide dispersant and VI improving compositions which exhibit good thermal stability.

Accordingly, it is a purpose of this invention to provide dispersants and dispersant VI improvers having polymeric structures which permit highly selective control of the degree of unsaturation and consequent functionalization. Unique materials can also be obtained by chemical modification of the polymers of this invention since the polymers can be selectively modified at controllable sites, such as at random sites or at the terminal ends of the molecules.

It is an additional purpose of this invention to provide a method for the production of dispersants and dispersant VI improvers from polymers having controlled amounts of unsaturation incorporated randomly in an otherwise saturated backbone. In contrast to EPDM-based dispersants, the level of unsaturation can be inexpensively and easily controlled, e.g., from 1% to 50%, to provide a wide variation in functionalizability.

It is a further purpose of the invention to provide dispersant and VI improving polymers having narrow molecular weight distributions and a concomitant lack of undesirable by-products, thereby providing more precisely tailored dispersant and/or VI improving properties.

It is still a further purpose of this invention to provide dispersants having improved engine performance.

SUMMARY OF THE INVENTION

The invention provides dispersant and dispersant Viscosity index (VI) improvers which include polymers of conjugated dienes which have been hydrogenated, functionalized, optionally modified, and post treated. The dispersancy and VI improving properties of the compositions of the invention may be controlled by controlling the size of the polymers and the extent and distribution of their functionalization. Accordingly, these substances are termed throughout "dispersant substances".

In one embodiment of the invention, there is provided a dispersant substance for modifying the dispersancy or viscometric properties of a lubricant fluid, in which the dispersant substance includes a copolymer of two different conjugated dienes. In this case, the first conjugated diene includes at least one relatively more substituted conjugated diene having at least five carbon atoms and the formula:

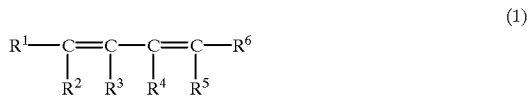

(1)

wherein $R^1$—$R^6$ are each hydrogen or a hydrocarbyl group, provided that at least one of $R^1$—$R^6$ is a hydrocarbyl group, and also provided that, after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups.

The second conjugated diene in the dispersant substances of this embodiment includes at least one relatively less substituted conjugated diene which is different from the first conjugated diene and has at least four carbon atoms and the formula:

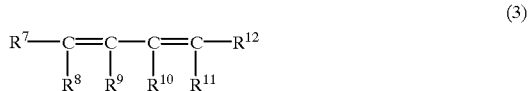

(3)

wherein $R^7$—$R^{12}$ are each hydrogen or a hydrocarbyl group, provided that, after polymerization, the unsaturation of the polymerized conjugated diene of formula (3) has the formula:

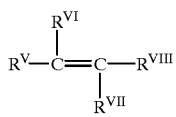
(4)

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

Following polymerization the diene copolymer is selectively hydrogenated and subsequently functionalized to provide a functionalized copolymer having at least one polar functional group.

The functionalized copolymer is optionally modified by reaction with a Lewis base selected from the group consisting of a monoamine, polyamine, polyhydroxy compound, reactive polyether, or a combination thereof.

The copolymer is then post treated with a post treating agent, for example a boron-containing compound.

In a preferred embodiment, the dispersant substance includes a polymer in which the first and second conjugated dienes are polymerized as a block copolymer including at least two alternating blocks:

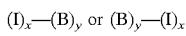
$(I)_x$—$(B)_y$ or $(B)_y$—$(I)_x$

In this case, the block (I) includes at least one polymerized conjugated diene of formula (1), while the block (B) includes at least one polymerized conjugated diene of formula (3). In addition, x is the number of polymerized monomer units in block (I) and is at least 1, and y is the number of polymerized monomer units in block (B) and is at least 25. It should be understood throughout that x and y are defined relative to blocks in a linear block copolymer or blocks in an arm or segment of a branched or star-branched copolymer in which the arm or segment has substantially linear structure.

Preferably, in the block copolymers of this embodiment, x is from about 1 to about 600, and y is from about 30 to about 4,000, more preferably x is from about 1 to about 350, and y is from about 30 to about 2,800. While larger values for x and y are generally related to larger molecular weights, polymers which have multiple blocks and star-branched polymers typically will have molecular weights which are not well represented in the values of x and y for each block.

Alternatively, the dispersant substance includes the first and second conjugated dienes polymerized as a random copolymer. The dispersant substance may include the first and second conjugated dienes polymerized as a branched or star-branched copolymer.

The copolymers useful according to this embodiment typically have a molecular weight of at least about 2,000. Preferably, the molecular weight of these polymers is from about 2,000 to about 1,000,000, more preferably from about 5,000 to about 500,000.

The molecular weight of a polymer of the invention is generally associated with the physical properties it exhibits when employed as a dispersant or dispersant VI improver. Typically, polymers having lower molecular weights are employed as dispersants, while VI-improving properties and relative thickening power are associated with polymers having higher molecular weights and correspondingly greater viscosity. For purposes of discussion, polymers of the invention having molecular weights in the range of from about 2,000 to about 20,000 may be classified as dispersants, polymers having molecular weights of from about 20,000 to about 50,000 may be classified as dispersants with VI-improving properties, and polymers having molecular weights of about 50,000 or more may be classified as dispersant VI improvers.

In the dispersant substances of the invention, the copolymer is preferably selectively hydrogenated. It is preferred that the unsaturation of formula (4) be substantially completely hydrogenated, thereby retaining substantially none of the original unsaturation of this type, while the unsaturation of formula (2) is substantially retained (i.e., the residual unsaturation after hydrogenation), in at least an amount which is sufficient to permit functionalization of the copolymer.

After the hydrogenation reaction, the Iodine Number for the residual unsaturation of formula (2) is generally from about 50% to about 100% of the Iodine Number prior to the hydrogenation reaction. More preferably, after hydrogenation, the Iodine Number for the residual unsaturation of formula (2) is about 100% of the Iodine Number prior to the hydrogenation reaction.

After the hydrogenation reaction, the Iodine Number for the residual unsaturation of formula (4) is from about 0% to about 10% of the Iodine Number prior to the hydrogenation reaction. More preferably, after the hydrogenation reaction, the Iodine Number for the residual unsaturation of formula (4) is from about 0% to about 0.5% of the Iodine Number prior to the hydrogenation reaction. Most preferably, after the hydrogenation reaction, the Iodine Number for the residual unsaturation of formula (4) is from about 0% to about 0.2% of the Iodine Number prior to the hydrogenation reaction.

The conjugated diene of formula (1) preferably includes a conjugated diene such as isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof. More preferably, the conjugated diene of formula (1) includes isoprene, myrcene, 2,3-dimethyl-butadiene or 2-methyl-1,3-pentadiene. Still more preferably, the conjugated diene of formula (1) includes isoprene.

Preferably, the conjugated diene of formula (3) includes 1,3-butadiene, 1,3-pentadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof. More preferably, the conjugated diene of formula (3) includes 1,3-butadiene, 1,3-pentadiene, or 1,3-hexadiene. Still more preferably, the conjugated diene of formula (3) includes 1,3-butadiene.

Generally, when the conjugated diene includes substantial amounts of 1,3-butadiene, the polymerized butadiene includes a mixture of 1,4- and 1,2-units. The preferred structures contain at least about 25% of the 1,2-units. More preferably, the structures contain from about 30% to about 90% of the 1,2-subunits. Most preferably, the structures contain from about 45% to about 65% of the 1,2-units.

To provide dispersancy, the selectively hydrogenated polymer is chemically modified (functionalized) to provide a polymer having at least one polar functional group, such as, but not limited to, halogen, epoxy, hydroxy, amino, nitrilo, mercapto, imido, carboxy, and sulfonic acid groups of combinations thereof. The functionalized polymers can be further modified to give a more desired type of functionality.

In a preferred case, the selectively hydrogenated polymer is functionalized by a method which includes: reacting the selectively hydrogenated polymer with an unsaturated carboxylic acid (or derivative thereof, such as maleic anhydride) to provide an acylated polymer, and then reacting the acylated polymer with a monoamine, a polyamine, a polyhydroxy compound, a reactive polyether, or a combination thereof.

The modified polymer is contacted with one or more post treating agents.

Any of the dispersant substances of the invention may include a functionalized polymer of the invention distributed in a carrier fluid such as a synthetic or mineral oil, to provide a dispersant concentrate. The dispersant concentrates generally include the polymer in an amount of from about 5% wt. to about 90% wt., more preferably from about 10% wt. to about 70% wt., of the dispersant substance, depending upon the molecular weight of the polymer.

The dispersant substances may further include at least one additive selected from the group consisting of antioxidants, pour point depressants, detergents, dispersants, friction modifiers, anti-wear agents, anti-foam agents, corrosion and rust inhibitors, Viscosity index improvers, and the like.

The invention further provides a method of modifying the dispersancy or viscometric properties of a fluid such as a lubricant. The method includes admixing with a fluid an amount of a dispersant substance of the invention which is sufficient to provide a dispersant-modified fluid having dispersancy or viscometric properties which are altered from the original fluid. Preferably, the method involves admixing the dispersant substance in an amount of from about 0.001% wt. to about 20% wt., more preferably from about 0.1% wt. to about 10% wt., and most preferably from about 0.5% wt. to about 7% wt., of the dispersant-modified fluid. Typically, the method of the invention is employed to modify lubricating oils and normally liquid fuels; such as motor oils, transmission fluids, hydraulic fluids, gear oils, aviation oils, and the like. In addition, the method may further include admixing with the fluid at least one additive such as antioxidants, pour point depressants, detergents, dispersants, friction modifiers, anti-wear agents, anti-foam agents, corrosion and rust inhibitors, viscosity index improvers, and the like.

The invention also provides a dispersant-modified fluid, such as a hydrocarbon fluid, having modified dispersancy or viscometric properties. In this embodiment, the dispersant-modified fluid typically includes a mineral or synthetic oil and a dispersant substance of the invention. Preferably, the dispersant-modified fluid of the invention includes a dispersant substance in an amount of from about 0.001% wt. to about 20% wt., more preferably from about 0.1% wt. to about 10% wt., and most preferably from about 0.5% wt. to about 7% wt., of the modified lubricating fluid. The dispersant-modified fluid preferably includes a mineral or synthetic lubricating oil or a normally liquid fuel; such as motor oils, transmission fluids, hydraulic fluids, gear oils, aviation oils, and the like. These dispersant-modified fluids may further include at least one additive such as antioxidants, pour point depressants, detergents, dispersants, friction modifiers, anti-wear agents, anti-foam agents, corrosion and rust inhibitors, viscosity index improvers, and the like.

The polymers are prepared under anionic polymerization conditions. Following polymerization, the polymers of the invention are selectively hydrogenated to provide a controlled amount and extent of residual unsaturation. After the selective hydrogenation reaction, the hydrogenation catalyst is removed from the polymer and the polymer is chemically modified or functionalized to impart desirable characteristics for the dispersant substances of the invention.

Accordingly, as a result of the invention, there are now provided dispersants, dispersants with VI-improving properties, and dispersant VI improvers prepared by polymerization of conjugated dienes, followed by selective hydrogenation and functionalization. These dispersant substances of the invention possess numerous advantages, including improved engine performance, controlled molecular weight, controlled molecular weight distribution, controlled polymer structure, variable and controlled amounts and distribution of functionality, superior thermal stability, potentially permitting reduced treat levels and yielding benefits such as improved viscometric properties.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE INVENTION

The polymeric dispersants of the invention, typically having lower molecular weights, can be employed in any lubricant or fuel composition that requires a dispersant to control the deposition of sludge particles on, for example, engine parts. Other polymeric substances of the invention, typically those having higher molecular weights, may be employed for their VI- improving properties in any lubricant fluid which may benefit from a modification of its viscometric properties. These compounds may also find a variety of uses in addition to lubricant additives, such as adhesives, sealants, impact modifiers, and the like.

As noted above, traditional dispersants have been polybutenes functionalized via an ene reaction with maleic anhydride followed by imidization with a polyamine. The polybutenes are typically 500–2,000 in molecular weight. With one olefin per polybutene molecule, the number of potential functional groups per chain is limited to one. Consequently, the molecular weight of polybutene may not exceed 2,000 if the desired functionality/hydrocarbon ratio is to be maintained.

By contrast, with this invention, the amount of residual unsaturation can be controllably varied. As a result, the amount of functionality one wishes to incorporate is quite flexible. In addition, the molecular weight of the polymer backbone is not limited to 2,000. Higher molecular weight polymers can be prepared and functionalized such that the same functionality/hydrocarbon ratio that is found in the traditional dispersant is maintained if so desired. Moreover, with this invention, the position of the functionality is not limited to the end of the polymer chain as it is with polybutenes. Instead, a variety of options is now available, including, for example, randomly along the backbone, at one end, at both ends, or in the center, of the polymer chain.

If a polymer according to the invention is of sufficiently high molecular weight (e.g., 20,000–50,000), it will exhibit increased thickening power and viscosity index-improving (VI-improving) properties, as well as sludge dispersing ability. Hence, the use of these materials may permit reduction in use of both traditional dispersants and VI. If materials are prepared with backbones that are 50,000 in molecular weight, the functionalized versions can be classified as dispersant VI improvers or VI improvers with dispersant properties. Their dispersant capabilities are outstanding for dispersant VI improvers.

In one embodiment, the present invention provides polymers including at least two different conjugated dienes, wherein one of the dienes is more substituted in the 2, 3, and/or 4 carbon positions than the other diene. The more substituted diene produces vinylidene, tri-, or tetra-substituted double bonds after polymerization. Hydrogenation of the material is done selectively so as to saturate the lesser substituted olefins, which primarily arise from the lesser substituted diene, while leaving a portion of the more substituted conjugated olefins behind for functionalizing.

In this embodiment, the more substituted conjugated diene will have at least five (5) carbon atoms and the following formula:

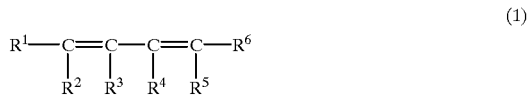

(1)

wherein $R^1$—$R^6$ are each hydrogen (H) or a hydrocarbyl group, provided that at least one of $R^1$—$R^6$ is a hydrocarbyl group. After polymerization, the unsaturation in the polymerized conjugated diene of formula (1) has the following formula:

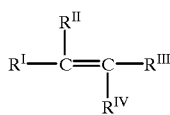

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups. Examples of conjugated dienes of formula 1 include isoprene, 2,3-dimethylbutadiene, 2-methyl-1,3-pentadiene, myrcene, and the like. Isoprene is highly preferred.

The lesser substituted conjugated diene in this embodiment differs from the other diene in that it has at least four (4) carbon atoms and the following formula:

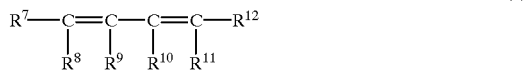

(3)

wherein $R^7$—$R^{12}$ are each hydrogen or a hydrocarbyl group. After polymerization, the unsaturation in the polymerized conjugated diene of formula (3) has the following formula:

(4)

wherein $R^V$, $R^{VI}$, $R^{VII}$ and $R^{VIII}$ are each hydrogen (H) or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group. Examples of the conjugated diene of formula (3) include 1,3-butadiene, 1,3-pentadiene, 2,4-hexadiene, and the like. A highly preferred conjugated diene of formula 3 is 1,3-butadiene.

An exception to this scheme would be when a tetra-substituted diene, e.g., 2,3-dimethylbutadiene, is used for the more substituted component. When this occurs, a tri-substituted olefin, e.g. isoprene, may be used for the lesser substitued component, such that one or both of $R^V$ and $R^{VI}$ are hydrogen and both $R^{VII}$ and $R^{VIII}$ are hydrocarbyl.

It will be apparent to those skilled in the art that in the original unsaturation of formula (2), $R^I$, $R^{II}$, $R^{III}$ and $R^{IV}$ may all be hydrocarbyl groups, whereas in the original unsaturation of formula (4) at least one of $R^V$, $R^{VI}$, $R^{VII}$ and $R^{VIII}$ must be a hydrogen.

The hydrocarbyl group or groups in the formula (1) to (4) are the same or different and they are substituted or unsubstituted alkyl, alkenyl, cycloalkyl, cycloalkenyl, aryl, alkaryl, or aralkyl groups, or any isomers thereof.

The copolymers of this embodiment are prepared by anionically polymerizing a diene of formula (1) at a level of from about 0.5% wt. to about 25% wt.,and a diene of formula (3) at a level of from about 75% wt. to about 99.5% wt., in a hydrocarbon solvent using an alkyllithium catalyst. The two monomers can be polymerized in block, tapered block, or random fashion. Since the polymerization is anionic, the molecular weight distribution of these copolymers is typically very narrow, generally ranging from about 1.01 to about 1.20, and the molecular weight is determined by the ratio of monomer to initiator and/or by the presence of coupling agents. The monomers (1) and (3) may be polymerized either simultaneously or in stepwise fashion depending on the desired position of the remaining unsaturation after hydrogenation. If random positioning of the unsaturation is desired, both monomers are reacted together to give a random copolymer. If it is desirable to have the functionality on only one end, then the monomers are reacted in stepwise fashion, the order being determined as desired, to provide a diblock copolymer. If functionality is needed on both ends, then a conjugated diene of formula (1) is polymerized first, followed by a diene of formula (3). To the living anion, a coupling agent, e.g., phenyl benzoate or methyl benzoate, is then added to yield a desired triblock copolymer. Alternatively, a diene of formula (1) may be added to the living diblock to give the triblock.

A fourth approach would allow the functionality to be positioned in the center of the polymer chain. In this case, a diene of formula (3) is polymerized first, followed by a diene of formula (1). Then a triblock is formed by addition of a coupling agent or by addition of more diene of formula (3). In addition, combinations of the above approaches may be employed.

The invention can include polymers of differing microstructures. The presence of polar modifier increases the activity of the catalyst and, therefore, increase the level of 1,2-microstructure over 1,4-microstructure in polybutadiene, for example. The percentage of vinyl obtained is directly proportional to the concentration of the modifier employed. Since the reaction temperature also plays a role in determining the microstructure of polybutadiene, the level of modifier must be chosen taking into account the combined effects. Antkowiak et al., *Temperature and Concentration Effects on Polar-modified Alkyl Lithium Polymerizations and Copolymerizations, Journal of Polymer Science: Part A*-1, 10:1319–34 (1972), incorporated herein by reference have presented a way for quickly determining the proper conditions for preparation of any 1,2-microstructure content within a range of from about 10% to about 80%. Use of this method or any others to achieve the desired microstructure will be known to anyone who is skilled in the art.

The dispersants and dispersant VI improvers of the invention can include different polymer macrostructures. Polymers may be prepared and utilized having linear and/or nonlinear, e.g., star-branched, macrostructures. The star-branched polymers can be prepared by addition of divinylbenzene or the like to the living polymer anion. Lower levels of branching can be obtained through the use of tri-functional or tetra-functional coupling agents, such as tetrachlorosilane.

In all embodiments of this invention, whenever a reference is made to the "original double bond" or the "original unsaturation" of the block or random polymer (or copolymer), it is understood to mean the double bond(s) in the polymer prior to the hydrogenation reaction. By contrast, the terms "residual double bond(s)" and "residual unsaturation", as used herein, refer to the unsaturated group (s), typically excluding aromatic unsaturation, present in the copolymer after the selective hydrogenation reaction.

The molecular structure of the original or residual double bonds can be determined in any conventional manner, as is known to those skilled in the art, e.g., by infrared (IR) or nuclear magnetic resonance (NMR) analysis. In addition, the total original or residual unsaturation of the polymer can be quantified in any conventional manner, e.g., by reference to the Iodine Number of the polymer.

In any polymers of any of the embodiments of this invention, the microstructure of the polymerized conjugated diene of formula (3) must be such that the polymer is not excessively crystalline after the selective hydrogenation reaction. That is, after the selective hydrogenation reaction the polymer must retain its elastomeric properties, e.g., the polymer should contain not more than about 10% of polyethylene crystallinity. Generally, problems of crystallinity occur only when the polymer includes polymerized 1,3-butadiene. Limiting polymeric crystallinity may be accomplished in various ways. For example, this is accomplished by introducing side branches into the polymerized conjugated dienes of formula (1) and/or (3), e.g., by controlling the microstructure of 1,3-butadiene if it is the predominant monomer in the diene of formula (3); by using a mixture of dienes of formula (3) containing less than predominant amounts of 1,3-butadiene; or by using a single diene of formula (3), other than 1,3-butadiene. More particularly, if the conjugated diene(s) of formula (3) is predominantly (at least 50% by mole) 1,3-butadiene, the side branches are introduced into the polymer by insuring that the polymerized diene of formula (3) contains a sufficient amount of the 1,2-units to prevent the selectively hydrogenated polymer from being excessively crystalline. Thus, if the conjugated diene of formula (3) is predominantly (at least 50% by mole, e.g., 100% by mole) 1,3-butadiene, the polymerized diene of formula (3), prior to the selective hydrogenation reaction, must contain not more than about 75% wt., preferably from about 10% wt. to about 70% wt., and most preferably from about 35% wt. to about 55% wt. of the 1,4-units, and at least about 25% wt., preferably from about 30% wt. to about 90% wt., and most preferably from about 45% wt. to about 65% wt. of the 1,2-units. If the polymerized diene(s) of formula (3) contains less than 50% by mole of 1,3-butadiene, e.g., 1,3-pentadiene is used as the only diene of formula (3), the microstructure of the polymerized diene of formula (3) prior to the selective hydrogenation reaction is not critical since, after hydrogenation, the resulting polymer will contain substantially no crystallinity.

In all embodiments of the invention, mixtures of dienes of formula (1) or (3) may be used to prepare block copolymers $(I)_x$—$(B)_y$, or any of the random copolymers or star-branched block and random polymers of the invention. Similarly, mixtures of aryl-substituted olefins may also be used to prepare block, random, or star-branched copolymers of this invention. Accordingly, whenever a reference is made herein to a diene of formula (1) or (3), or to an aryl-substituted olefin, it may encompass more than one diene of formula (1) or (3), respectively, and more than one aryl-substituted olefin.

The block copolymers of this invention comprise two or more alternating blocks, identified above. Linear block copolymers having two blocks and block copolymers having three or more blocks are contemplated herein.

The block polymers useful according to the invention typically include at least one block which is substantially completely saturated, while also including at least one block containing controlled levels of unsaturation providing a hydrocarbon elastomer with selectively positioned unsaturation for subsequent functionalization. For the copolymers prepared from two different conjugated dienes, it has been found that the two dienes in the copolymers hydrogenate at different rates, permitting selective control of the placement of residual unsaturation.

The many variations in composition, molecular weight, molecular weight distribution, relative block lengths, microstructure, branching, and $T_g$ (glass transition temperature) attainable with the use of anionic techniques employed in the preparation of our polymers will be obvious to those skilled in the art.

While not wishing to limit the molecular weight range of liquid elastomers prepared according to our invention, the minimum molecular weight for these liquid polymers is at least about 2,000, preferably about 2,000 to about 100,000, and most preferably about 5,000 to about 35,000. The star-branched block and random copolymers of this invention may have substantially higher molecular weights and still retain liquid properties. The minimum weight for solid polymers of this invention is at least about 50,000 to about 1,000,000. The block copolymers of this invention are functionalizable. Without wishing to be bound by any theory of operability, it is believed that they can be functionalized in a controlled manner through the unsaturated groups on the terminal or the interior blocks to provide dispersants and dispersant VI improvers having almost uniform distribution of molecular weights. The star-branched and linear versions of the random copolymers and homopolymers of this invention are also functionalizable.

All numerical values of molecular weight given in this specification and the drawings are of number average molecular weight ($M_n$).

The invention will be described hereinafter in terms of the embodiments thereof summarized above. However, it will be apparent to those skilled in the art, that the invention is not limited to these particular embodiments, but, rather, it covers all the embodiments encompassed by the broadest scope of the description of the invention.

Copolymers From at Least Two Dissimilar Conjugated Dienes

In this embodiment of the invention, there are provided copolymers of two dissimilar conjugated dienes, preferably isoprene and 1,3-butadiene. The two monomers can be polymerized by anionic polymerization process in either a block, tapered block, or random fashion.

The copolymers of this embodiment include a first conjugated diene having at least five (5) carbon atoms and the following formula:

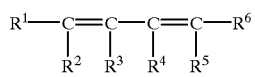 (1)

wherein $R^1$—$R^6$ are each hydrogen or a hydrocarbyl group, provided that at least one of $R^1$—$R^6$ is a hydrocarbyl group, and further provided that, when polymerized, the structure of the double bond in the polymerized conjugated diene of formula (1) has the following formula:

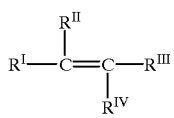 (2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups. In the double bond of the polymerized conjugated diene of formula (2), $R^I$, $R^{II}$, $R^{III}$ and $R^{IV}$ may all be hydrocarbyl groups.

The polymers of this embodiment also include a second conjugated diene, different from the first conjugated diene, having at least four (4) carbon atoms and the following formula:

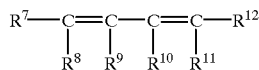 (3)

wherein $R^7$—$R^{12}$ are each hydrogen or a hydrocarbyl group, provided that the structure of the double bond in the polymerized conjugated diene of formula (3) has the following formula:

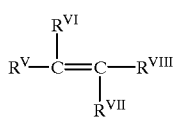 (4)

wherein $R^V$, $R^{VI}$, $R^{VII}$ and $R^{VIII}$ are each hydrogen (H) or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group.

Following polymerization the diene copolymer of this embodiment is preferably functionalized by a method which includes selectively hydrogenating the copolymer to provide a selectively hydrogenated copolymer, followed by functionalizing the selectively hydrogenated copolymer to provide a functionalized copolymer having at least one polar functional group.

The polymers of this embodiment include a first conjugated diene of formula (1) in an amount of from about 0.5% wt. to about 30% wt., and a second conjugated diene in an amount of from about 70% wt. to about 99.5% wt. Preferably, a first conjugated diene is included in an amount of from about 1% wt. to about 25% wt., and a second conjugated diene in an amount of from about 75% to about 99% wt. More preferably, a first conjugated diene is included in an amount of from about 5% wt. to about 20% wt., and a second conjugated diene is included in an amount of from about 80% to about 95% wt.

The polymers of this embodiment include block copolymers having at least two alternating blocks:

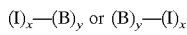

In this case, the polymer includes at least one block (I). The block (I) is a block of at least one polymerized conjugated diene of formula (1) as described above. These block copolymers also include at least one polymerized block (B). The block (B) is a block of at least one polymerized conjugated diene of formula (3) described above.

In the block copolymers of this embodiment, x is at least 1, preferably from about 1 to about 600, and most preferably from about 1 to about 350. The above definition of x means that each of the (I) blocks is polymerized from at least 1, preferably about 1–600, and more preferably about 1–350, monomer units.

In the block copolymers of this embodiment, y is at least 25, preferably from about 30 to about 4,000, more preferably from about 30 to about 2,800. The above definition of y means that each of the (B) blocks is polymerized from at least 25, preferably about 30–4,000, and more preferably about 30–2,800, monomer units.

The block copolymer comprises about 0.5 to about 25%, preferably about 1 to about 20% by wt. of the (I) blocks, and about 80 to about 99.5%, preferably about 80 to about 99% by wt. of the (B) blocks.

In any of the copolymers of this embodiment, the structures of the double bonds defined by formula (2) and (4) are necessary to produce copolymers which can be selectively hydrogenated in the manner described herein, to produce the selectively hydrogenated block and random copolymers of this invention.

The hydrocarbyl group or groups in the formula (1) and (2) are the same or different and they are substituted or unsubstituted alkyl, alkenyl, cycloalkyl, cycloalkenyl, aryl, alkaryl, or aralkyl groups, or any isomers thereof. Suitable hydrocarbyl groups are alkyls of 1–20 carbon atoms, alkenyls of 1–20 carbon atoms, cycloalkyls of 5–20 carbon atoms, aryls of 6–12 carbon atoms, alkaryls of 7–20 carbon atoms or aralkyls of 7–20 carbon atoms. Examples of suitable alkyl groups are methyl, ethyl, propyl, butyl, pentyl, hexyl, heptyl, octyl, decyl, methyl-decyl or dimethyl-decyl. Examples of suitable alkenyl groups are ethenyl, propenyl, butenyl, pentenyl or hexenyl. Examples of suitable cycloalkyl groups are cyclohexyl or methylcyclohexyl. Examples of suitable cycloalkenyl groups are 1-, 2-, or 3-cyclohexenyl or 4-methyl-2-cyclohexenyl. Examples of suitable aryl groups are phenyl or diphenyl. Examples of suitable alkaryl groups are 4-methyl-phenyl (p-tolyl) or p-ethyl-phenyl. Examples of suitable aralkyl groups are benzyl or phenethyl. Suitable conjugated dienes of formula (1) used to polymerize the (I) block are isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3 pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene, or mixtures thereof, preferably isoprene, myrcene, 2,3-dimethyl-butadiene, or 2-methyl-1, 3-pentadiene, and most preferably isoprene.

The hydrocarbyl group or groups in the formula (3) may or may not be the same as those in formula (4). These hydrocarbyl groups are the same as those described above in conjunction with the discussion of the hydrocarbyl groups of formula (1) and (2). Suitable monomers for the (B) block are 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene, or mixtures thereof, preferably 1,3-butadiene, 1,3-pentadiene, 2,4-hexadiene, or 1,3-hexadiene, and most preferably it is 1,3-butadiene. It is generally preferred that each of the (B) blocks is polymerized from a single monomer.

The scope of this embodiment, and of any other embodiments of the invention wherein the block (B) is used, also encompasses polymers wherein the block (B) may comprise copolymers of one or more conjugated diene of formula (3) and controlled amounts (about 0.3 to about 30 mole %) of an aryl-substituted olefin, e.g., styrene or other suitable monomers (such as alkylated styrene, vinyl naphthalene, or alkylated vinyl naphthalene) incorporated for control of glass transition temperature ($T_g$), density, solubility parameters and refractive index. Similarly, the scope of this embodiment also encompasses polymers wherein the block (B) may be comprised of copolymers of one or more conjugated diene of formula (3) and any other anionically polymerizable monomer capable of polymerizing with the conjugated diene of formula (3). Similar considerations also apply in the case of the (I) block(s), which can include similar styrene/diene copolymers.

The copolymer is polymerized by anionic polymerization, discussed in detail below. As will be apparent to those skilled in the art, the block copolymer of this embodiment contains at least two alternating blocks, (I)—(B) or (B)—(I), referred to herein as diblocks. The block copolymer of this embodiment may contain three alternating blocks, e.g., (I)—(B)—(I), referred to herein as triblocks or triblock units, but it may contain an unlimited number of blocks. The functionalization of any of these copolymers is conducted in a conventional manner and is described below.

After the (I)—(B) copolymer is polymerized, it is subjected to a selective hydrogenation reaction during which the polymerized conjugated dienes of formula (3) of the copolymer are selectively hydrogenated to such an extent that they contain substantially none of the original unsaturation, while the polymerized conjugated dienes of formula (1) of the copolymer retain a sufficient amount of their original unsaturation to permit functionalization.

Generally, for a copolymer wherein the conjugated dienes of formula (1) and (3) are polymerized to provide unsaturation of formula (2) and (4), respectively, as discussed above, the Iodine Number for the unsaturation of formula (2) after the selective hydrogenation reaction is from about 20% to about 100%, preferably from about 50% to about 100%, and most preferably about 100%, of the Iodine Number prior to the selective hydrogenation reaction; and for the unsaturation of formula (4) it is from about 0% to about 10%, preferably from about 0% to about 0.5%, and most preferably from about 0% to about 0.2%, of the Iodine Number prior to the selective hydrogenation reaction. The Iodine Number, as is known to those skilled in the art, is defined as the theoretical number of grams of iodine which will add to the unsaturation in 100 grams of olefin and is a quantitative measure of unsaturation.

In this embodiment of the invention, although the microstructure of the (I) blocks is not critical and may consist of 1,2-, 3,4- and/or 1,4-units, schematically represented below for the polyisoprene blocks, when a polar compound is used during the polymerization of the (I) block, the (I) blocks comprise primarily (at least about 50% wt.) 3,4-units, the rest being primarily (less than about 50% wt.) 1,4-units; when the polar compound is not used during the polymerization of the (I) block, the (I) blocks comprise primarily (about 80% wt.) 1,4-units, the rest being primarily 1,2- and 3,4- units.

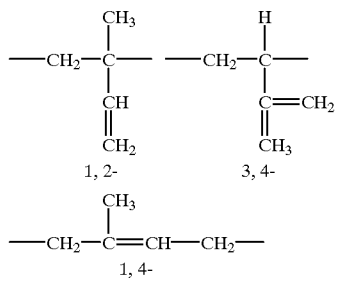

The microstructure of the (B) blocks, when the predominant monomer used to polymerize the (B) blocks is 1,3-butadiene, should be a mixture of 1,4- and 1,2- units schematically shown below for the polybutadiene blocks:

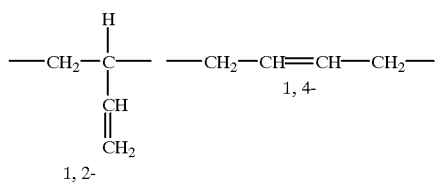

since the hydrogenation of the predominantly 1,4-microstructure produces a crystalline polyethylene segment. The microstructure of the (I) and (B) blocks (as well as of the polymerized conjugated dienes of formula (1) or (3) in any polymers of this invention) is controlled in a conventional manner, e.g., by controlling the amount and nature of the polar compounds used during the polymerization reaction, and the reaction temperature. In one particularly preferred embodiment, the (B) block contains about 50% of the 1,2- and about 50% of the 1,4-microstructure. If the (B) block is poly-1,3-butadiene, the hydrogenation of the (B) segment containing from about 50% to about 60% of the 1,2-microstructure content produces an elastomeric center block which is substantially an ethylene-butene-1 copolymer having substantially no crystallinity. If the (B) block is polymerized from 1,3-pentadiene, the microstructure is not critical.

The terms "1,2-", "1,4-", and "3,4-microstructure" or "units" as used in this application refer to the products of polymerization obtained by the 1,2-, 1,4- and 3,4-, respectively, mode of addition of monomer units.

We surprisingly discovered that the polymerized conjugated dienes of formula (3), e.g., the dienes employed in (B) blocks, of the polymers of this invention are selectively hydrogenated in our hydrogenation process much faster than the polymerized conjugated dienes of formula (1), e.g., the dienes used in the (I) blocks. This is not evident from the teachings of Falk, discussed above, because Falk teaches that double bonds of the di-substituted 1,4-polybutadiene units are hydrogenated selectively in the presence of double bonds of the tri-substituted 1,4-polyisoprene units (which hydrogenate very slowly). We surprisingly discovered that the di-substituted double bonds of the 1,4-polybutadiene units are hydrogenated along with the monosubstituted double bonds of the 1,2-polybutadiene units, while the di-substituted double bonds of the 3,4-polyisoprene units are hydrogenated at a much slower rate than the aforementioned polybutadienes. Thus, in view of Falk's disclosure it is surprising that the di-substituted double bonds of the 1,4-polybutadiene units are hydrogenated selectively in the presence of the di-substituted double bonds of the 3,4-polyisoprene units. This is also surprising in view of the teachings of Hoxmeier, Published European Patent application, Publication No. 0 315 280, who discloses that the di-substituted double bonds of the 1,4-polybutadiene units, monosubstituted double bonds of the 1,2-polybutadiene units and di-substituted double bonds of the 3,4-polyisoprene units are hydrogenated simultaneously at substantially the same rates. For example, for the block copolymers of this invention, wherein the (I) block is polyisoprene and the (B) block is polybutadiene, Fourier Transform Infrared (FTIR) analysis of selectively hydrogenated block copolymers of the invention, such as I—B—I triblock polymers, indicates that the hydrogenation of the double bonds of the 1,2-polybutadiene units proceeds most rapidly, followed by the hydrogenation of the double bonds of the 1,4-polybutadiene units. Infrared absorptions caused by these groups disappear prior to appreciable hydrogenation of the polyisoprene units.

Accordingly, by controlling the amount and placement of 1,2- versus 1,4-microstructure, as well as the amount and placement of polyisoprene units, it is now possible to control the amount and placement of unsaturation remaining in the polymers after hydrogenation. It follows that the amount and placement of functionalization of the polymeric dispersants of the invention is also controllable to an extent not possible previously.

After the block copolymer is prepared, it is subjected to a selective hydrogenation reaction to hydrogenate primarily the (B) block(s). The selective hydrogenation reaction and the catalyst are described in detail below. After the hydrogenation reaction is completed, the selective hydrogenation catalyst is removed from the block copolymer, and the polymer is isolated by conventional procedures, e.g., alcohol flocculation, steam stripping of solvent, or non-aqueous solvent evaporation. An antioxidant, e.g., Irganox 1076 (from Ciba-Geigy), is normally added to the polymer solution prior to polymer isolation.

Random Copolymers

Random copolymers of this invention have controlled amounts of unsaturation incorporated randomly in an otherwise saturated backbone. In contrast to EPDM, the level of unsaturation can be easily controlled, e.g., to produce polymers having Iodine Number of from about 5 to about 100, to provide a wide variation in the degree of functionalization.

In one embodiment, the random copolymers are polymerized from the same monomers used to polymerize the block copolymers $(I)_x$—$(B)_y$, described elsewhere herein. In particular, the random copolymers may be made by polymerizing at least one conjugated diene of formula (1) with at least one conjugated diene of formula (3), both defined above. This random copolymer contains from about 1.0% to about 40%, preferably from about 1.0% to about 20%, by mole of the polymerized conjugated diene of formula (1) and from about 60% to about 99%, preferably from about 80% to about 99% by mole of the polymerized conjugated diene of formula (3). Suitable conjugated dienes of formula (1) are exemplified above. The most preferred conjugated diene of formula (1) for the copolymerization of these random copolymers is isoprene. Suitable conjugated dienes of formula (3) are also exemplified above. 1,3-butadiene is the most preferred conjugated diene of formula (3) for the polymerization of the random copolymer of this embodiment. Thus, most preferably, in this embodiment, the random copolymer is polymerized from isoprene and 1,3-butadiene, and it contains from about 1% wt. to about 20% wt. of the isoprene units and from about 80% wt. to about 99% wt. of the butadiene units. The isoprene units have primarily (i.e., from about 50% wt. to about 90% wt.) the 3,4-microstructure.

The random copolymers are subjected to the selective hydrogenation reaction discussed above for the block copolymers, during which polymerized conjugated diene units of formula (3) are substantially completely hydrogenated, while the conjugated diene units of formula (1) are hydrogenated to a substantially lesser extent, i.e., to such an extent that they retain a sufficient amount of their original unsaturation to functionalize the copolymer, thereby producing dispersants and dispersant VI improvers having random unsaturation proportional to the unsaturation in the polymerized dienes of formula (1). For example, for random copolymer polymerized from a diene of formula (1) and a different diene of formula (3), the Iodine Number before selective hydrogenation for the polymer is about 450. After selective hydrogenation, the Iodine Number for the polymer is from about 10 to about 50, with most of the unsaturation being contributed by the diene of formula (1).

The hydrogenated polymers are functionalized in the same manner as set forth for block copolymers.

Star-Branched Polymers

The invention is also directed to star-branched block and random polymers. The star-branched block polymers are made from any combination of blocks (I) and (B), defined above.

The star-branched (I)—(B) block polymers comprise from about 0.5% wt. to about 25% wt., preferably from about 1% wt. to about 20% wt., of the (I) blocks, and from about 75% wt. to about 99.5% wt., preferably from about 80% wt. to about 99% wt., of the (B) blocks.

The star-branched block polymers are selectively hydrogenated in the selective hydrogenation process of this invention to such an extent that blocks (B) contain substantially none of the original unsaturation, while each of the blocks (I) respectively, retains a sufficient amount of the original unsaturation of the conjugated dienes present in these blocks to functionalize the star-branched block polymers. Thus, for the I—(B) star-branched block polymer, after the selective hydrogenation reaction, the Iodine Number for the (I) blocks is from about 10% to about 100%, preferably from about 25% to about 100%, more preferably from about 50% to about 100%, and most preferably about 100%, of the Iodine Number prior to the selective hydrogenation reaction; and for the (B) blocks it is from about 0% to about 10%, preferably from about 0% to about 0.5%, of the Iodine Number prior to the selective hydrogenation reaction.

The star-branched random polymers are made from any combination of at least one diene of formula (1) and at least one diene of formula (3), different from the diene of formula (1), or from any combination of at least one aryl-substituted olefin and at least one diene of formula (1) or (3), all of which are the same as those discussed above. The star-branched random polymers of the dienes of formula (1) and (3), which must be different from each other, comprise from about 0.5% wt. to about 25% wt., preferably from about 1% wt. to about 20% wt., of the diene of formula (1), and from about 75% wt. to about 99.5% wt., preferably from about 80% wt. to about 99% wt., of the diene of formula (3). The star-branched random polymers of the aryl-substituted olefin and the diene of formula (1) or (3) comprise from about 0.5% wt. to about 50% wt., preferably from about 1% wt. to about 25% wt., of the aryl-substituted olefin, and from about 50% wt. to about 99.5% wt., preferably from about 75% wt. to about 99% wt., of the diene of formula (1) or (3).

The star-branched random diene polymers are also selectively hydrogenated in the selective hydrogenation process of this invention to such an extent that the polymerized dienes of formula (3) contain substantially none of the original unsaturation, while the polymerized dienes of formula (1) retain a sufficient amount of the original unsaturation to functionalize the star-branched random polymers. Thus, for the star-branched random polymer of the conjugated diene of formula (1) and a different diene of formula (3), both identified above, the Iodine Number for the polymerized diene of formula (1), after the selective hydrogenation reaction, is from about 10% to about 100%, preferably from about 25% to about 100%, more preferably from about 50% to about 100%, and most preferably about 100%, of the Iodine Number prior to the selective hydrogenation reaction; and for the polymerized diene of formula (3) it is from about 0% to about 10%, preferably from about 0% to about 0.5%, of the Iodine Number prior to the selective hydrogenation reaction.

Polymerization Reaction

The polymers of this invention are polymerized by any known polymerization processes, preferably by an anionic polymerization process. Anionic polymerization is well known in the art and it is utilized in the production of a variety of commercial polymers. An excellent comprehensive review of the anionic polymerization processes appears in the text *Advances in Polymer Science 56, Anionic Polymerization*, pp. 1–90, Springer-Verlag, Berlin, Heidelberg, New York, Tokyo 1984 in a monograph entitled *Anionic Polymerization of Non-polar Monomers Involving Lithium,* by R. N. Young, R. P. Quirk and L. J. Fetters, incorporated herein by reference. The anionic polymerization process is conducted in the presence of a suitable anionic catalyst (also known as an initiator), such as n-butyl-lithium, sec-butyl-lithium, t-butyl-lithium, sodium naphthalide or, cumyl potassium. The amount of the catalyst and the amount of the monomer in the polymerization reaction dictate the molecular weight of the polymer. The polymerization reaction is conducted in solution using an inert solvent as the polymerization medium, e.g., aliphatic hydrocarbons, such as hexane, cyclohexane, or heptane, or aromatic solvents, such as benzene or toluene. In certain instances, inert polar solvents, such as tetrahydrofuran, can be used alone as a solvent, or in a mixture with a hydrocarbon solvent.

The polymerization process will be exemplified below for the polymerization of one of the embodiments of the invention, e.g., a triblock of polyisoprene-polybutadiene-polyisoprene. However, it will be apparent to those skilled in the art that the same process principles can be used for the polymerization of all polymers of the invention.

The process, when using a lithium-based catalyst, comprises forming a solution of the isoprene monomer in an inert hydrocarbon solvent, such as cyclohexane, modified by the presence therein of one or more polar compounds selected from the group consisting of ethers, thioethers, and tertiary amines, e.g., tetrahydrofuran. The polar compounds are necessary to control the microstructure of the butadiene center block, i.e., the content of the 1,2-structure thereof. The higher the content of the polar compounds, the higher will be the content of the 1,2-structure in these blocks. Since the presence of the polar compound is not essential in the formation of the first polymer block with many initiators unless a high 3,4-structure content of the first block is desired, it is not necessary to introduce the polar compound at this stage, since it may be introduced just prior to or together with the addition of the butadiene in the second polymerization stage. Examples of polar compounds which may be used are dimethyl ether, diethyl ether, ethyl methyl ether, ethyl propyl ether, dioxane, diphenyl ether, dipropyl ether, tripropyl amine, tributyl amine, trimethyl amine, triethyl amine, and N-N-N'-N'-tetramethyl ethylene diamine. Mixtures of the polar compounds may also be used. The amount of the polar compound depends on the type of the polar compound and the polymerization conditions as will be apparent to those skilled in the art. The effect of polar compounds on the polybutadiene microstructure is detailed in Antkowiak et al. The polar compounds also accelerate the rate of polymerization. If monomers other than 1,3-butadiene, e.g., pentadiene, are used to polymerize the central blocks (B), polar compounds are not necessary to control the microstructure because such monomers will inherently produce polymers which do not possess crystallinity after hydrogenation.

When the alkyl lithium-based initiator, a polar compound and an isoprene monomer are combined in an inert solvent, polymerization of the isoprene proceeds to produce the first terminal block whose molecular weight is determined by the ratio of the isoprene to the initiator. The living polyisoprenyl anion formed in this first step is utilized as the catalyst for further polymerization. At this time, butadiene monomer is introduced into the system and block polymerization of the second block proceeds, the presence of the polar compound now influencing the desired degree of branching (1,2-structure) in the polybutadiene block. The resulting product is a living diblock polymer having a terminal anion and a lithium counterion. The living diblock polymer serves as a catalyst for the growth of the final isoprene block, formed when isoprene monomer is again added to the reaction vessel to produce the final polymer block, resulting in the formation of the I—B—I triblock. Upon completion of polymerization, the living anion, now present at the terminus of the triblock, is destroyed by the addition of a proton donor, such as methyl alcohol or acetic acid. The polymerization reaction is usually conducted at a temperature of between about 0° C. and about 100° C., although higher temperatures can be used. Control of a chosen reaction temperature is desirable since it can influence the effectiveness of the polar compound additive in controlling the polymer microstructure. The reaction temperature can be, for example, from about 50° C. to about 80° C. The reaction pressure is not critical and varies from about atmospheric to about 100 psig.

If the polar compounds are utilized prior to the polymerization of the first (I) segment, (I) blocks with high 3,4-unit content are formed. If polar compounds are added after the initial (I) segment is prepared, the first (I) segment will possess a high percentage of 1,4-microstructure (which is tri-substituted), and the second (I) segment will have a high percentage of 3,4-microstructure.

The production of triblock polymers having a high 1,4-unit content on both of the terminal (I) blocks is also possible by the use of coupling techniques illustrated below for a polyisoprene-polybutadiene-polyisoprene block copolymer:

```
        RLi
ISOPRENE -----> 1,4-POLYISOPRENE
POLAR COMPOUND
----------------> 1,4-POLYISOPRENE-POLYBUTADIENE
BUTADIENE
COUPLING AGENT 1,4-POLYISOPRENE-POLYBUTADIENE-1,4-POLYISOPRENE
--------------->
```

The substitution of myrcene for the isoprene during the polymerization of the (I) blocks insures the incorporation of a high proportion of tri-substituted double bonds, even in the presence of polar compounds since myrcene contains a pendant tri-substituted double bond which is not involved in the polymerization process. In a coupling process, similar to that described above, block polymers containing polyisoprene end blocks (or any other polymerized monomer suitable for use in the (I) block) having a high 3,4-microstructure content can be obtained by adding the polar compound prior to the isoprene (or another monomer) polymerization.

The use of the coupling technique for the production of triblock polymers reduces the reaction time necessary for the completion of polymerization, as compared to sequential addition of isoprene, followed by butadiene, followed by isoprene. Such coupling techniques are well known and utilize coupling agents such as esters, $CO_2$, iodine, dihaloalkanes, silicon tetrachloride, divinyl benzene, alkyl trichlorosilanes and dialkyl dichlorosilanes. The use of tri- or tetra-functional coupling agents, such as alkyl trichlorosilanes or silicon tetrachloride, permits the formation of macromolecules having 1- or 2-main chain branches, respectively. The addition of divinyl benzene as a coupling agent has been documented to produce molecules having up to 20 or more separately joined segments.

The use of some of the coupling agents provides a convenient means of producing star-branched block and random polymers. The star-branched block polymers are made from any combination of blocks (I) and (B), defined above. The star-branched random polymers are made from any combination of at least one diene of formula (1) and at least one diene of formula (3), different from the diene of formula (1), or from at least one aryl-substituted olefin, at least one diene of formula (1) and at least one diene of formula (3), different from the diene of formula (1). The molecular weight of the star-branched block and random copolymers will depend on the number of branches in each such copolymer, as will be apparent to those skilled in the art. Suitable coupling agents and reactions are disclosed in the following references which are incorporated herein by reference: U.S. Pat. Nos. 3,949,020; 3,594,452; 3,598,887; 3,465,065; 3,078,254; 3,766,301; 3,632,682; 3,668,279; and Great Britain patent Nos. 1,014,999; 1,074,276; 1,121,978.

Selective Hydrogenation

Following polymerization, selective hydrogenation of the polymer may be accomplished using techniques similar to those known in the art. A preferred method and catalyst are described in U.S. Pat. No. 5,187,236, the disclosure of which is incorporated herein by reference. The procedure and catalyst are described in greater detail below. In general, however, the previously described polymers can be contacted with hydrogen and a hydrogenation catalyst synthesized from a transition metal compound, typically nickel or cobalt, and an organometallic reducing agent, e.g., triethylaluminum. The hydrogenation proceeds at temperatures typically not in excess of about 40° C. and at pressures of from about 30 psi to about 200 psi. Generally, the polymers are hydrogenated such that substantially all of the unsaturation in formula (4) is removed, while much of that from formula (2) is retained.

The selective hydrogenation reaction will also be described below using a triblock of polyisoprene-polybutadiene-polyisoprene as an example. However, it will be apparent to those skilled in the art that any polymers of this invention can be selectively hydrogenated in the same manner.

In Example II below, the block copolymer is selectively hydrogenated to saturate the middle (polybutadiene) block. The method of selectively hydrogenating the polybutadiene block is similar to that of Falk, *Coordination Catalysts for the Selective Hydrogenation of Polymeric Unsaturation, Journal of Polymer Science: Part A*-1, 9:2617–23 (1971), but it is conducted with a novel hydrogenation catalyst and process used herein. Any other known selective hydrogenation methods may also be used, as will be apparent to those skilled in the art, but it is preferred to use the method described herein. In summary, the selective hydrogenation method preferably used herein comprises contacting the previously-prepared block copolymer with hydrogen in the presence of the novel catalyst composition.

The novel hydrogenation catalyst composition and hydrogenation process are described in detail in previously cited application Ser. No. 07/466,136. The hydrogenation catalyst composition is synthesized from at least one transition metal compound and an organometallic reducing agent. Suitable transition metal compounds are compounds of metals of Group IVb, Vb, VIb or VIII, preferably IVb or VIII of the Periodic Table of the Elements, published in *Lange's Handbook of Chemistry*, 13th Ed., McGraw-Hill Book Company, New York (1985) (John A. Dean, ed.). Non-limiting examples of such compounds are metal halides, e.g., titanium tetrachloride, vanadium tetrachloride; vanadium oxytrichloride, titanium and vanadium alkoxides, wherein the alkoxide moiety has a branched or unbranched alkyl radical of 1 to about 20 carbon atoms, preferably 1 to about 6 carbon atoms. Preferred transition metal compounds are metal carboxylates or alkoxides of Group IVb or VIII of the Periodic Table of the Elements, such as nickel (II) 2-ethylhexanoate, titanium isopropoxide, cobalt (II) octoate, nickel (II) phenoxide and ferric acetylacetonate.

The organometallic reducing agent is any one or a combination of any of the materials commonly employed to activate Ziegler-Natta olefin polymerization catalyst components containing at least one compound of the elements of Groups Ia, IIa, IIb, IIIa, or IVa of the Periodic Table of the Elements. Examples of such reducing agents are metal alkyls, metal hydrides, alkyl metal hydrides, alkyl metal halides, and alkyl metal alkoxides, such as alkyllithium compounds, dialkylzinc compounds, trialkylboron compounds, trialkylaluminum compounds, alkylaluminum halides and hydrides, and tetraalkylgermanium compounds. Mixtures of the reducing agents may also be employed. Specific examples of useful reducing agents include n-butyllithium, diethylzinc, di-n-propylzinc, triethylboron, diethylaluminumethoxide, triethylaluminum, trimethylaluminum, triisobutylaluminum, tri-n-hexylaluminum, ethylaluminum dichloride, dibromide, and dihydride, isobutyl aluminum dichloride, dibromide, and dihydride, diethylaluminum chloride, bromide, and hydride, di-n-propylaluminum chloride, bromide, and hydride, diisobutylaluminum chloride, bromide and hydride, tetramethylgermanium, and tetraethylgermanium. Organometallic reducing agents which are preferred are Group IIIa metal alkyls and dialkyl metal halides having 1 to about 20 carbon atoms per alkyl radical. More preferably, the reducing agent is a trialkylaluminum compound having 1 to about 6 carbon atoms per alkyl radical. Other reducing agents which can be used herein are disclosed in Stevens et al., U.S. Pat. No. 3,787,384, column 4, line 45 to column 5, line 12 and in Strobel et al., U.S. Pat. No. 4,148,754, column 4, line 56 to column 5, line 59, the entire contents of both of which are incorporated herein by reference. Particularly preferred reducing agents are metal alkyl or hydride derivatives of a metal selected from Groups Ia, IIa and IIIa of the Periodic Table of the Elements, such as n-butyl lithium, sec-butyl lithium, n-hexyl lithium, phenyl-lithium, triethylaluminum, tri-isobutylaluminum, trimethyl-aluminum, diethylaluminum hydride and dibutylmagnesium.

The molar ratio of the metal derived from the reducing agent to the metal derived from the transition metal compound will vary for the selected combinations of the reducing agent and the transition metal compound, but in general it is about 1:1 to about 12:1, preferably about 1.5:1 to about 8:1, more preferably about 2:1 to about 7:1, and most preferably about 2.5:1 to about 6:1. It will be apparent to those skilled in the art that the optimal ratios will vary depending upon the transition metal and the organometallic agent used, e.g., for the trialkylaluminum/nickel(II) systems, the preferred aluminum:nickel molar ratio is about 2.5:1 to about 4:1, for the trialkylaluminum/cobalt(II) systems, the preferred aluminum: cobalt molar ratio is about 3:1 to about 4:1, and for the trialkylaluminum/titanium(IV) alkoxides systems, the preferred aluminum: titanium molar ratio is about 3:1 to about 6:1.

The mode of addition and the ratio of the reducing agent to the transition metal compound are important in the production of the novel hydrogenation catalyst having superior selectivity, efficiency and stability, as compared to prior art catalytic systems. During the synthesis of the catalysts it is preferred to maintain the molar ratio of the reactants used to synthesize the catalyst substantially constant. This can be done either by the addition of the reducing agent, as rapidly as possible, to a solution of the transition metal compound, or by a substantially simultaneous addition of the separate streams of the reducing agent and the transition metal compound to a catalyst synthesis vessel in such a manner that the selected molar ratios of the metal of the reducing agent to the metal of the transition metal compound are maintained substantially constant throughout substantially the entire time of addition of the two compounds. The time required for the addition must be such that excessive pressure and heat build-up are avoided, i.e., the temperature should not exceed about 80° C. and the pressure should not exceed the safe pressure limit of the catalyst synthesis vessel.

In a preferred embodiment, the reducing agent and the transition metal compound are added substantially simultaneously to the catalyst synthesis vessel in such a manner that the selected molar ratio of the reducing agent to the transition metal compound is maintained substantially constant during substantially the entire time of the addition of the two compounds. This preferred embodiment permits the control of the exothermic reaction so that the heat build-up is not excessive, and the rate of gas production during the catalyst synthesis is also non excessive—accordingly, the gas build-up is relatively slow. In this embodiment, carried out with or without a solvent diluent, the rate of addition of the catalyst components is adjusted to maintain the synthesis reaction temperature at or below about 80° C., which promotes the formation of the selective hydrogenation catalyst. Furthermore, the selected molar ratios of the metal of the reducing agent to the metal of the transition metal compound are maintained substantially constant throughout the entire duration of the catalyst preparation when the simultaneous mixing technique of this embodiment is employed.

In another embodiment, the catalyst is formed by the addition of the reducing agent to the transition metal compound. In this embodiment, the timing and the order of addition of the two reactants is important to obtain the hydrogenation catalyst having superior selectivity, efficiency and stability. Thus, in this embodiment, it is important to add the reducing agent to the transition metal compound in that order in as short a time period as practically possible. In this embodiment, the time allotted for the addition of the reducing agent to the transition metal compound is critical for the production of the novel catalyst. The term "as short a time period as practically possible" means that the time of addition is as rapid as possible, such that the reaction temperature is not higher than about 80° C. and the reaction pressure does not exceed the safe pressure limit of the catalyst synthesis vessel. As will be apparent to those skilled in the art, that time will vary for each synthesis and will depend on such factors as the types of the reducing agents, the transition metal compounds and the solvents used in the synthesis, as well as the relative amounts thereof, and the type of the catalyst synthesis vessel used. For purposes of illustration, a solution of about 15 mL of triethylaluminum in hexane should be added to a solution of nickel(II) octoate in mineral spirits in about 10–30 seconds. Generally, the addition of the reducing agent to the transition metal compound should be carried out in about 5 seconds (sec) to about 5 minutes (min), depending on the quantities of the reagents used. If the time period during which the reducing agent is added to the transition metal compound is prolonged, e.g., more than 15 minutes, the synthesized catalyst is less selective, less stable, and may be heterogeneous.

In the embodiment wherein the reducing agent is added as rapidly as possible to the transition metal compound, it is also important to add the reducing agent to the transition metal compound in the aforementioned sequence to obtain the novel catalyst. The reversal of the addition sequence, i.e., the addition of the transition metal compound to the reducing agent, or the respective solutions thereof, is detrimental to the stability, selectivity, activity, and homogeneity of the catalyst and is, therefore, undesirable.

In all embodiments of the hydrogenation catalyst synthesis, it is preferred to use solutions of the reducing agent and the transition metal compound in suitable solvents, such as hydrocarbon solvents, e.g., cyclohexane, hexane, pentane, heptane, benzene, toluene, or mineral oils. The solvents used to prepare the solutions of the reducing agent and of the transition metal compound may be the same or different, but if they are different, they must be compatible with each other so that the solutions of the reducing agent and the transition metal compound are fully soluble in each other.

The hydrogenation process comprises contacting the unsaturated polymer to be hydrogenated with an amount of the catalyst solution containing about 0.1 to about 0.5, preferably about 0.2 to about 0.3 mole percent of the transition metal based on moles of the polymer unsaturation. The hydrogen partial pressure is generally from about 5 psig to about several hundred psig, but preferably it is from about 10 psig to about 100 psig. The temperature of the hydrogenation reaction mixture is generally from about 0° C. to about 150° C., preferably from about 25° C. to about 80° C., more preferably from about 30° C. to about 60° C., since higher temperatures may lead to catalyst deactivation. The length of the hydrogenation reaction may be as short as 30 minutes and, as will be apparent to those skilled in the art, depends to a great extent on the actual reaction conditions employed. The hydrogenation process may be monitored by any conventional means, e.g., infra-red spectroscopy, hydrogen flow rate, total hydrogen consumption, or any combination thereof.

Upon completion of the hydrogenation process, unreacted hydrogen is either vented or consumed by the introduction of the appropriate amount of an unsaturated material, such as 1-hexene, which is converted to an inert hydrocarbon, e.g., hexane. Subsequently, the catalyst is removed from the resulting polymer solution by any suitable means, selected depending on the particular process and polymer. For a low molecular weight material, for example, catalyst residue removal may consist of a treatment of the solution with an oxidant, such as air, and subsequent treatment with ammonia and optionally methanol in amounts equal to the molar amount of the metals (i.e., the sum of the transition metal and the metal of the reducing agent) present in the hydrogenation catalyst to yield the catalyst residues as a filterable precipitate, which is filtered off. The solvent may then be removed by any conventional methods, such as vacuum stripping, to yield the product polymer as a clear, colorless fluid.

Alternatively, and in a preferred embodiment, upon completion of the hydrogenation reaction, the mixture is treated with ammonia in the molar amount about equal to that of the metals (i.e., the sum of the transition metal and the metal of the reducing agent) and aqueous hydrogen peroxide, in the molar amount equal to about one half to about one, preferably one half, of the amount of the metals. Other levels of the ammonia and peroxide are also operative, but those specified above are particularly preferred. In this method, a precipitate forms, which may be filtered off as described above.

In yet another alternative method, the catalyst may be removed by extraction with an aqueous mineral acid, such as sulfuric, phosphoric, or hydrochloric acid, followed by washing with distilled water. A small amount of a material commonly used as an aid in removing transition metal-based catalysts, such as a commercially available high molecular weight diamine, e.g., Jeffamine D-2000 from Huntsman, may be added to aid in phase separation and catalyst removal during the extractions. The resultant polymer solution is then dried over a drying agent, such as magnesium sulfate, separated from the drying agent and the solvent is then separated by any conventional methods, such as vacuum stripping, to yield a polymer as a clear fluid. Other methods of polymer isolation, such as steam or alcohol flocculation, may be employed depending upon the hydrogenated polymer properties.

After hydrogenation and purification is complete, the polymer can be functionalized and used in the lubricant compositions of the invention: the liquids will serve as dispersants and the solids as dispersant VI improvers.

Functionalization of the Polymers

The unsaturated terminal blocks of the block polymers of this invention can be chemically modified or functionalized to provide benefits which enhance the dispersancy and viscosity improving qualities of the materials of the invention. Such benefits may be obtained through methods similar to those employed for the modification of existing commercial materials, such as polyisobutylene or EPDM.

Following the selective hydrogenation step, the remaining sites of unsaturation may be chemically modified. Such methods include reacting the unsaturated groups in the polymer with any of various reagents to produce functional groups, such as halogen, hydroxyl, epoxy, sulfonic acid, mercapto, acrylate or carboxyl groups. Functionalization methods are well known in the art.

A preferred chemical modification method involves reaction of the polymer with an unsaturated carboxylic acid and/or derivatives, such as acrylic acid, maleic acid, fumaric acid, maleic anhydride, methacrylic acid, esters of these acids, and the like. Most preferably, maleic anhydride is used for the chemical modification of unsaturation. Numerous methods are known for the chemical modification of polyisobutylene and EPDM via the ene reaction. Methods are also known for the reaction of maleic anhydride with EPDM via a radical reaction in the presence of a radical initiator. These methods can be adapted to incorporate the unsaturated carboxylic acid derivatives into the polymeric dispersants of the invention.

Subsequent to the acylation reaction (or other suitable chemical modifications as outlined above), the chemically modified polymers may be reacted with a Lewis base, such as a monoamine, a polyamine, a polyhydroxy compound, a reactive polyether, or a combination thereof. Amines which are useful for this modification reaction are characterized by the presence of at least one primary (i.e., $H_2N-$) or secondary (i.e., $HN=$) amino group. The monoamines and polyamines can be aliphatic amines, cycloaliphatic amines, heterocyclic amines, aromatic amines, or hydroxyamines. Preferably, the polyamines contain only one primary or secondary amine, with the remaining amines being tertiary (i.e., $-N=$) or aromatic amines. The amination can be accomplished by heating the maleic anhydride-modified diene polymer to about 150° C. in the presence of the amine, followed by stripping off the water. A useful monoamine is ethanol amine. Useful polyamines include aminopropylmorpholine and tetraethylenepentamine. Useful polyhydroxy compounds include ethylene glycol and pentaerythritol. Useful reactive polyethers include polyethers which contain hydroxy or amino groups which will react with the modified polymer, such as polyethylene glycol monoalcohol. In addition, when the modified polymers react with an aromatic polyamine, the resultant dispersant has improved antioxidant properties.

In a preferred functionalization of diene copolymers, the selectively hydrogenated copolymer is functionalized with functional groups selected from among halogens IV, epoxies, sulfonic acids, mercapto acid and/or derivatives and carboxylic acid derivatives, and subsequently modified further by reacting with a monoamine, a polyamine, a polyhydroxy compound, a reactive polyether, or a combination thereof.

The ene reaction of maleic anhydride with materials of the invention can be performed on neat polymers or solutions of the polymers in light mineral oil or polyalphaolefin at temperatures of from about 150° C. to about 250° C., typically under an inert atmosphere. Such modification of the polymers of any embodiments of our invention occurs readily, since the residual isoprene unsaturation, primarily of the 3,4-type, illustrated above, is known to be more reactive with maleic anhydride than are the internal bonds found in EPDM.

In addition, the selectively hydrogenated polymer may be functionalized by other methods which enhance the dispersancy, including but not limited to: grafting of heteroatom-containing olefins; formation of Mannich base condensates at the sites of unsaturation; hydroformylation/reductive amination; addition of nitrosamines or nitrosophenols; lithiation followed by reaction with electrophilic compounds capable of displacement or addition reactions to provide carboxy, nitrilo, or amino groups; 1,3-dipolar addition of nitrile oxides, nitrones, and the like; light catalyzed cycloaddition of activated olefins; and light catalyzed insertion reactions.

Grafting of heteroatom-containing olefins may be accomplished by reacting the polymer with a vinyl monomer in the presence of a free radical initiator, such as t-butylperoxybenzoate, to directly form a dispersant molecule. Nitrogen and/or oxygen-containing vinyl monomers, such as vinyl imidazole and maleic anhydride, may be used. The number of vinyl monomers appended to the polymer in this fashion can be from 1 to 20 or more per 10,000 molecular weight.

Suitable vinyl monomers are disclosed in U.S. Pat. Nos. 5,663,126; 5,140,075; 5,128,086; 4,146,489; 4,092,255; and 4,810,754, incorporated herein by reference.

Suitable free radical initiators are disclosed in U.S. Pat. Nos. 5,663,126 and 4,146,489, incorporated herein by reference.

Any conventional grafting method may be used. For example, the grafting may be performed by dissolving the polymer in a solvent, preferably a hydrocarbon solvent, adding a free radical initiator and a nitrogen and/or oxygen-containing vinyl monomer. The mixture is then heated to obtain a grafted polymer. The grafted polymer may be isolated by conventional methods. For example, the graft copolymer may be converted to a concentrate by evaporative distillation of solvent, non-reacted vinyl monomer, and reaction by-products. For ease of handling, a mineral oil diluent may be added before or after the evaporative procedure.

The grafted polymer may be further reacted with an amine, preferably containing at least one —NH group. Suitable amines include monoamines, polyamines, amino alcohols, amino acids or derivatives thereof, and amino terminated polyethers.

The selectively hydrogenated polymer may also be functionalized by a Mannich base condensation reaction or chemical modification followed by a Mannich base condensation reaction. The polymer is reacted with a phenol to provide a hydroxy aromatic functionalized polymer which is subsequently reacted with an aldehyde or aldehyde precursor and at least one amino or polyamino compound having at least one —NH group to form a dispersant molecule. The number of phenolic groups (Mannich condensates) per molecule can be from 1 to 20 or more per 10,000 molecular weight.

Useful amines in the preparation of the Mannich condensate dispersants of this invention include monoamines, polyamines, amino alcohols, amino acids or derivatives thereof, and amino terminated polyethers with the proviso that the amine has at least one —NH group.

Suitable aldehydes include $C_1$ to $C_{10}$ linear, cyclic or branched aldehydes.

Mannich base condensation reactions are described in U.S. Pat. Nos. 3,413,347; 3,697,574; 3,634,515; 3,649,229; 3,442,808; 3,798,165; 3,539,633; 3,725,277; 3,725,480; 3,726,882; 4,454,059; 5,102,566; and 5,663,130, incorporated herein by reference.

Alternatively, the selectively hydrogenated polymer may be functionalized by aminomethylation or hydroformylation followed by reductive amination. The polymer is reacted with carbon monoxide and hydrogen, in the presence of a transition metal catalyst to provide carbonyl derivatives of the polymer. The functionalized polymer is subsequently modified by reductive amination. Useful amines include, but are not limited to, monoamines, polyamines, amino alcohols, amino acids or derivatives thereof, and amino terminated polyethers with the proviso that the amine has at least one NH group. The number of suitable reaction sites per molecule can be from 1 to 20 or more per 10,000 molecular weight.

Aminomethylation and hydroformylation followed by reductive amination are described in U.S. Pat. Nos. 3,311,598; 3,438,757; 4,832,702; and 5,691,422, incorporated herein by reference.

The above description illustrates only some of the potentially valuable chemical modification of the polymers of this invention. The polymers of this invention provide a means for a wide variety of chemical modifications at selected sites in the polymer, e.g., at select ends, in the middle, or randomly, thereby presenting the opportunity to prepare materials previously impossible because of the lack of availability of such polymers. Some examples of well known chemical reactions which can be performed on polymers of this invention are found in E. M. Fettes, "Chemical Reactions of Polymers", *High Polymers*, Vol. 19, John Wiley, New York, (1964), incorporated herein by reference.

Post Treatment of the Polymers

Post treatment compositions of this invention include those formed by contacting the dispersants of this invention with one or more post-treating agents to give improved properties to finished lubricants. Such improved properties include enhanced performance in high temperature oxidation tests and in deposit and wear related full scale engine tests.

Suitable post-treating agents include boronating agents; phosphorylating agents; alkaline earth metal oxidating, sulfonating and carbonating agents; and IB and IIB metal oxidating, sulfating and sulfonating agents.

Suitable boronating agents or boron-containing compounds include boron acids, particularly boric acid or metaboric acid, boron oxide, boron oxide hydrate, boron esters, boron salts, particularly an ammonium borate, and boron halides.

Suitable phosphorylating agents include an inorganic acid of phosphorus, such as phosphorous acid and phosphoric acid, an anhydride thereof, a partial or complete sulfur analog thereof and an organic acid phosphate, such as 2-ethylhexyl acid phosphate.

Suitable alkaline earth oxidating, sulfonating and carbonating agents include calcium oxide, calcium sulfonate, calcium carbonate, barium oxide, barium sulfonate and barium carbonate.

Suitable IB and IIB metal oxidating, sulfating and sulfonating agents include zinc sulfate, zinc oxide, zinc sulfonate and cuprous oxide.

Post-treating agents and methods by which they can be employed in effecting post treatment of ashless dispersants are disclosed in U.S. Pat. Nos. 5,464,549 and 4,234,435 incorporated herein by reference.

Dispersant and VI-Improving Applications

The polymers of the invention, whether block copolymers, tapered block copolymers, branched and star branched polymers, or random copolymers, have been found to have an unexpected capacity to modify the dispersancy and/or viscometric properties of fluids, such as mineral and synthetic oil lubricants and normally liquid fuels. Accordingly, it is within the scope of the invention that the dispersant polymers of the invention be employed in dispersant substances which can be added to fluids to modify the dispersancy and/or viscometric properties of the fluids. The invention, thus, also includes a method of modifying or improving the dispersancy and/or viscometric properties of a fluid by admixing with the fluid a sufficient amount of a dispersant substance of the invention so as to obtain or provide a modified or improved fluid having modified or improved dispersancy and/or viscometric properties. Moreover, the invention also includes dispersant-modified or dispersant-improved fluids to which have been added a dispersant substance of the invention so as to modify the dispersancy and/or viscometric properties of the fluid.

The improvement of viscometric properties includes any one or more of the properties of fluids which are related to viscosity. The dispersant VI improvers of the invention specifically improve the viscosity index of such fluids. Viscosity index is a property characterizing the relationship between the viscosity of a fluid and temperature. Improvement in viscosity index is characterized by a decrease in the rate of change of viscosity per unit of temperature change. Typical properties which are modified or improved by the dispersant VI improvers of the invention include relative thickening power (RTP), borderline pumpability, permanent shear stability (DIN), temporary shear stability at low temperatures (CCS), and temporary shear stability at high temperatures (HTHS). Each of these properties can be determined or characterized by conventional methods.

The polymers of the invention may be employed as dispersants and/or dispersant VI improvers in a variety of lubricant fluids. Typically, such fluid is a mineral oil such as a mineral oil lubricant system, e.g., motor oils, automatic transmission fluids, tractor hydraulic fluids, gear oils, aviation oils, and the like. Other suitable applications include normally liquid fuels. The lubricant or fuel may be naturally occurring or synthetic, or a combination thereof. Natural oils include mineral oils obtained from petroleum, including distillate and residual lubricating oils, and the like. Synthetic oils can include synthetic hydrocarbon fluids e.g. PAOs, liquid esters, fluorocarbons, polyethers, polysilicones, and the like. The dispersants can be added to a lubricant or fuel formulation in any suitable and effective amount to modify the dispersancy and/or viscometric properties of the formulation. An exemplary broad range is from about 0.001% wt. to about 20% wt., preferably from about 0.1% wt. to about 10% wt., more preferably from about 0.5% wt. to about 7% wt., of the formulation.

The polymers of the invention can be supplied neat or as an oil concentrate for ease of handling. Typically, such dispersant concentrates include a polymer of the invention in an amount of from about 5% wt. to about 90% wt., preferably from about 10% wt. to about 70% wt., of the concentrate.

In addition to the polymers described in this invention, the dispersant formulations and the fluid formulations can further include one or more additional additives known to those skilled in the art. Such additives include, for example, antioxidants, pour point depressants, detergents, dispersants, friction modifiers, anti-wear agents, VI improvers, anti-foam agents, corrosion and rust inhibitors, etc. Indeed, it is among the advantages of the compositions of the invention that they are unusually efficient modifiers of dispersancy and/or viscometric properties, such that in many cases significantly less of these additives need be added to achieve a desired combination of fluid properties.

EXAMPLES

The following examples are intended to assist in a further understanding of the invention. The particular materials and conditions employed are intended to be further illustrative of the invention and are not limiting upon the reasonable scope thereof.

In all of the following examples, the experimental polymerization and functionalization work was performed with dried reactors and equipment and under strictly anaerobic conditions. Extreme care must be used to exclude air, moisture and other impurities capable of interfering with the delicate chemical balance involved in the synthesis of the polymers of this invention, as will be apparent to those skilled in the art.

Example I

Preparation of Dispersant Precursor Backbones

Using the procedure described in Example VII of U.S. Pat. No. 5,633,415, incorporated herein by reference, isoprene-butadiene diblock polymers having typical number average molecular weights as listed below are prepared:

| Polymer | Mn |
|---------|-------|
| A | 5000 |
| B | 10000 |
| C | 15000 |
| D | 20000 |

Example II

Selective Hydrogenation of the Polymer of Example I

The polymer solutions of Example I are each subjected to a selective hydrogenation procedure using a catalyst prepared by diethylaluminum ethoxide and cobalt octoate (3.5 to 1 molar ratio) and following general procedures as described in Example VIII of U.S. Pat. No. 5,633,415, incorporated herein by reference. The extent of hydrogenation is followed by Fourier Transfer Infrared (FTIR) and is continued until no absorption remains at 910cm$^{-1}$ and 990 cm$^{-1}$ (—1,2 polybutadiene structure) and essentially no residual trans double bonds are present as seen by disappearance of the 968 cm−1 absorption. The FTIR analysis of the polymers at the end of the selective hydrogenation typically indicates 0 to 10 trans polybutadiene double bonds and 50 to 100 vinylidene (—3,4 polyisoprene) double bonds remain normalized to 100,000 molecular weight polymer chain. That is, a 10,000 molecular weight polymer would typically have 0 to 1 residual trans double bonds and 5 to 10 vinylidene double bonds (for subsequent functionalization).

The hydrogenation catalyst is removed by washing, as described in U.S. Pat. No. 5,633,415, or by a filtration procedure preceded by precipitation of the catalyst with essentially stoichiometric levels of acetic acid and hydrogen peroxide. After catalyst removal, the polymers are isolated by removal of the solvent under reduced pressure to give polymers II-A, II-B, II-C, and II-D.

Example III

Maleic Modification of the Polymers of Example II

The polymers of Example II are dissolved in a diluent oil (e.g. low viscosity mineral oil or polyalphaolefin) to give fluid concentrate having 50% polymer content. Each of the concentrates, in turn, is reacted with a sufficient amount of maleic anhydride to give an acid number (based on neat polymer) of 35–40. This is equivalent to 6–7% maleic adduction to the polymer chain. The reaction is performed at approximately 200° C. and is monitored by FTIR and/or acid number titration of stripped samples. The time required for reaction is typically 3 to 20 hours. After reaction, any residual maleic anhydride is removed by vacuum stripping of the oil concentrate. The succinic anhydride modified polymers obtained, III-A, III-B, III-C and III-D are next treated with a polyamine to form the dispersants of this invention.

Example IV

Reaction of the Polymers of Example III with a Polyamine

The polymers of Example III are individually reacted with aminopropyl morpholine (APM) (1 mole per mole of anhydride) at elevated temperatures (100–200° C.) to form a morpholinopropyl succinimide adduct. Progress of the reaction is followed by monitoring water reaction product volume as well as disappearance of succinic anhydride absorption in FTIR coupled with appearance of typical imide absorption at about 1705 cm$^{-1}$. Any excess amine is removed by vacuum distillation and completeness of the reaction is confirmed by acid number titration and determination of total base number (TBN) by perchloric acid titration. Typical TBN values for the imidized polymers are 35 (based on neat polymer). The number of functional imides per molecules varies with molecular weight, and is typically:

| Polymer | Approximate Mn | Typical Functional groups per molecule |
| --- | --- | --- |
| IV-A | 5000+ | 3–3.5 |
| IV-B | 10000+ | 6–7 |
| IV-C | 15000+ | 9–10.5 |
| IV-D | 20000+ | 12–14 |

For ease of handling, the higher molecular weight polymers IV-C and IV-D can be further diluted with oil.

Example V

Post-treatment of the Dispersants of Example IV

The dispersants of Example IV show excellent performance at reduced treat rates in a variety of laboratory tests, as described in the U.S. Pat. No. 5,633,415, incorporated herein by reference. This example illustrates that further improvement can be gained by the addition of a boron containing additive (boric acid ester with a boron content of 5.5%) to the dispersants IV-A, IV-B, IV-C and IV-D.

The following tests illustrate the benefits of post-treatment of the listed dispersants with low levels of these compounds.

Hot Tube Test

Oxidative thermal stability is measured by the use of a hot tube test. In this test, air and formulated oil are fed at controlled rates through a small bore glass tube heated to 288° C. over a 16-hour period. The oil is collected and the amount of deposits present are measured by filtering a weighed amount of the effluent oil through a 0.8 um Millipore filter.

For this test, 2% (dry basis) of the listed dispersants are added to a fully formulated motor oil containing no other ashless dispersants. A comparison is made of deposit formation with and without added boron compound.

| Dispersant Type | Boron Additive (%) | Normalized Deposits |
| --- | --- | --- |
| IV-B | 0 | 1 |
| IV-B | 0.5 | 0.17 |
| IV-C | 0 | 1 |
| IV-C | 0.5 | 0.13 |
| IV-D | 0 | 1 |
| IV-D | 0.5 | 0.29 |

It can be seen that addition of a boron additive reduces deposit formation in this test by approximately 80%.

Blotter Test

The ability of the dispersants of this invention to disperse engine sludge was measured in a bench test where the test dispersant and a severe used oil from a Sequence VE engine test are mixed in a 1:2 ratio. The mixture is heated to 200° C. for 2 hours and allowed to cool to room temperature. Three drops of the mixture are then placed on Whatman No. 3031 chromatography paper. After 2 hours, the diameters of the inner ring of dispersed sludge and outer oil ring are measured. The rating is the diameter of the inner ring divided by the diameter of outer ring multiplied by 10. A rating of 10 would be the highest attainable value. Freshly prepared formulations of borated and non-borated dispersants give equivalent ratings.

In addition, retention of dispersancy in oil samples which have undergone the Hot Tube Test (above) is greater in dispersants which have been treated with a boron compound.

| Dispersant Type (%) | Boron Additive (%) | Blotter Rating Before Hot Tube | Rating After Hot Tube |
| --- | --- | --- | --- |
| IV-B (2) | (0) | 8.9 | 6.6 |
| IV-B (2) | (0.5) | 8.9 | 8.9 |

Differential Scanning Calorimetry (DSC)

Thermal oxidative stability can be measured by DSC. The dispersant (2%) in a formulated oil is heated as a thin film in air at 200° C. until an exothermic event is measured. A longer time to exotherm measurement is indicative of greater stability. A typical time for borated dispersants formulations was between 109 and 124 minutes. In contrast, non-borated dispersants took 67 to 93 minutes. The date below represents average values

| Dispersants Type (%) | Boron Additive (%) | Minutes to Exotherm |
|---|---|---|
| IV-B (2) | 0 | 84 |
| IV-B (2) | 0.5 | 114 |
| IV-D (2) | 0 | 85 |
| IV-D (2) | 0.5 | 121 |

The increased thermal-oxidative stability gained by treatment with the boron additive is readily seen.

Sequence III-E Engine Testing

Post treatment of disperants described in Example IV with a boron additive increases performance of fully formulated lubricants in a Sequence III-E engine test. Oil ring land deposits (ORLD) are reduced (higher rating number) and the average cam wear is diminished versus an untreated control.

| Dispersants Type (%) | Boron Additive (%) | ORLD Rating | Ave. Cam Wear |
|---|---|---|---|
| IV-D (2) | 0 | 4.19 | 24.5 |
| IV-D (2) | 0.5 | 5.48 | 2.5 |

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A dispersant substance for modifying the dispersancy or viscometric properties of a fluid, comprising:

a copolymer of a first conjugated diene and a second conjugated diene, wherein:

said first conjugated diene comprises at least one relatively more substituted conjugated diene having at least five carbon atoms and the formula:

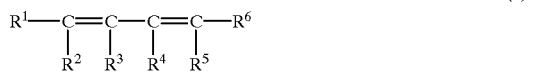

(1)

wherein $R^1$—$R^6$ are each hydrogen or a hydrocarbyl group, provided that at least one of $R^1$—$R^6$ is a hydrocarbyl group, provided that after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

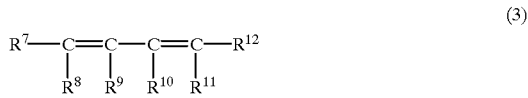

(3)

wherein $R^7$—$R^{12}$ are each hydrogen or a hydrocarbyl group, provided that after polymerization, the unsaturation of the polymerized conjugated diene of formula (3) has the formula:

(4)

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group; and wherein said copolymer has been functionalized by a method comprising:

selectively hydrogenating said copolymer to provide a selectively hydrogenated copolymer;

functionalizing said selectively hydrogenated copolymer to provide a functionalized copolymer having at least one polar functional group; and post treating the functionalized copolymer with a post-treating agent.

2. The dispersant substance of claim 1, wherein said functionalized copolymer is modified, prior to post treating, by reaction with a Lewis base selected from the group consisting of a monoamine, polyamine, polyhydroxy compound, reactive polyether, or a combination thereof.

3. The dispersant substance of claim 1, wherein said post-treating agent is a boron-containing compound.

4. The dispersant substance of claim 3, wherein said boron-containing compound is selected from the group consisting of boric acids, boron oxide, boron oxide hydrate, boron esters, boron salts, boron halides, or a combination thereof.

5. The dispersant substance of claim 4, wherein said boron-containing compound is boron ester.

6. The dispersant substance of claim 1, wherein said first and second conjugated dienes are polymerized as a block copolymer comprising at least two alternating blocks:

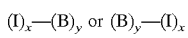

wherein:

the block (I) comprises at least one polymerized conjugated diene of formula (1);

the block (B) comprises at least one polymerized conjugated diene of formula (3);

x is the number of polymerized monomer units in block (I) and is at least 1, and y is the number of polymerized monomer units in block (B) and is at least 25.

7. The dispersant substance of claim 1, wherein said first and second conjugated dienes are polymerized as a branched or star-branched copolymer.

8. The dispersant substance of claim 1, wherein said copolymer has a molecular weight in the range of from about 2,000 to about 100,000.

9. The dispersant substance of claim 1, wherein said first conjugated diene is included in said polymer in an amount of from 1% to about 25% wt; and said second conjugated diene is included in said polymer in an amount of from about 75% wt. to about 99% wt.

10. The dispersant substance of claim 1, wherein after the selectively hydrogenating step, the Iodine Number for residual unsaturation of formula (2) is from about 50% to about 100% of the Iodine Number prior to the selectively hydrogenating step.

11. The dispersant substance of claim 1, wherein after the selectively hydrogenating step, the Iodine Number for residual unsaturation of formula (4) is from about 0% to about 10% of Iodine Number prior to the selectively hydrogenating step.

12. The dispersant substance of claim 1, wherein the conjugated diene of formula (1) comprises isoprene.

13. The dispersant substance of claim 12, wherein the conjugated diene of formula (3) comprises 1,3-butadiene.

14. The dispersant substance of claim 13, wherein each of the (B) blocks has from about 30% to about 90% of 1,2-subunits.

15. The dispersant substance of claim 1, wherein said functionalizing step provides a functionalized polymer having at least one functional group selected from the group consisting of halogen groups, hydroxyl groups, epoxy groups, sulfonic acid groups, mercapto groups, carboxylic acid derivative groups, and mixtures thereof.

16. The dispersant substance of claim 15, wherein said functional group comprises an unsaturated carboxylic acid and/or derivative group selected from the group consisting of acrylic acid, maleic acid, fumaric acid, maleic anhydride and methacrylic acid.

17. The dispersant substance of claim 16, wherein said functional group comprises maleic anhydride.

18. The dispersant substance of claim 1, wherein said polymer is distributed in a carrier fluid to provide a dispersant concentrate.

19. The dispersant substance of claim 18, wherein said polymer is included in an amount of from 5% to about 90% wt. of the dispersant concentrate.

20. The dispersant substance of claim 1, further comprising at least one additive selected from the group consisting of antioxidants, pour point depressants, detergents, dispersants, friction modifiers, anti-wear agents, anti-foam agents, corrosion and rust inhibitors and viscosity index improvers.

21. The dispersant substance of claim 2, wherein said polyamine comprises an aminopropylmorpholine.

22. A method of modifying the dispersancy or viscometric properties of a fluid, comprising:

admixing with a fluid an amount of dispersant substance sufficient to provide a dispersant-modified fluid having modified dispersant or viscometric properties; wherein said dispersant substance comprises:

a copolymer of a first conjugated diene and a second conjugated diene, wherein:

said first conjugated diene comprises at least one relatively more substituted conjugated diene having at least five carbon atoms and the formula:

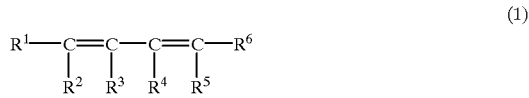

(1)

wherein $R^1$—$R^6$ are each hydrogen or a hydrocarbyl group, provided that at least one of $R^1$—$R^6$ is a hydrocarbyl group, provided that after polymerization, the unsaturation of the polymerized conjugated diene of formula (1) has the formula:

(2)

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

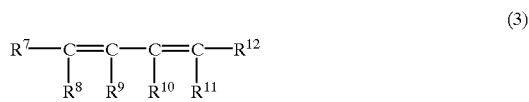

(3)

wherein $R^7$—$R^{12}$ are each hydrogen or a hydrocarbyl group, provided that after polymerization, the unsaturation of the polymerized conjugated diene of formula (3) has the formula:

(4)

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group; and wherein said copolymer has been functionalized by a method comprising:
selectively hydrogenating said copolymer to provide a selectively hydrogenated copolymer;
functionalizing said selectively hydrogenated copolymer to provide a functionalized copolymer having at least one polar functional group: and
post treating the functionalized copolymer with a post-treating agent.

23. The method of claim 22, comprising modifying the functionalized copolymer, prior to post treating, by reaction with a Lewis base selected from the group consisting of a monoamine, polyamine, polyhydroxy compound, reactive polyether, or a combination thereof.

24. The method of claim 22, comprising admixing said dispersant substance in an amount of from about 0.001% wt. to about 20% wt. of said dispersant-modified fluid.

25. The method of claim 22, comprising admixing said dispersant substance in an amount of from about 0.1% wt. to about 10% wt. of said dispersant-modified fluid.

26. The method of claim 22, comprising admixing said dispersant substance in an amount of from about 0.5% wt. to about 5% wt. of said dispersant-modified fluid.

27. The method of claim 22, wherein said fluid is selected from the group consisting of motor oils, transmission fluids, hydraulic fluids, gear oils, aviation oils, normally liquid fuels and lubricants.

28. The method of claim 22, further comprising admixing with said fluid at least one additive selected from the group consisting of antioxidants, pour point depressants, detergents, dispersants, friction modifiers, anti-wear agents, anti-foam agents, corrosion and rust inhibitors, viscosity index improvers, and the like.

29. A dispersant-modified fluid having modified dispersancy or viscometric properties comprising:
    a fluid; and
    a dispersant substance comprising;
        a copolymer of a first conjugated diene and a second conjugated diene, wherein:
            said first conjugated diene comprises at least one relatively more substituted conjugated diene having at least five carbon atoms and the formula:

$$R^1-C(R^2)=C(R^3)-C(R^4)=C(R^5)-R^6 \tag{1}$$

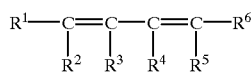

wherein $R^1$—$R^6$ are each hydrogen or a hydrocarbyl group, provided that at least one of $R^1$—$R^6$ is a hydrocarbyl group, provided that after polymerization, the unsaturation of the polymerized conjugated diene of formula (1) has the formula:

$$(2)$$

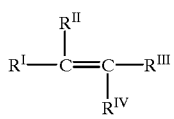

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; and said second conjugated diene comprises at least one relatively less substituted conjugated diene different from the first conjugated diene and having at least four carbon atoms and the formula:

$$(3)$$

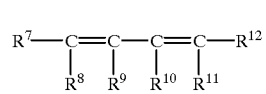

wherein $R^7$—$R^{12}$ are each hydrogen or a hydrocarbyl group, provided that after polymerization, the unsaturation of the polymerized conjugated diene of formula (3) has the formula:

$$(4)$$

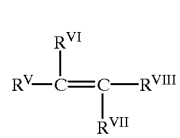

wherein $R^V$, $R^{VI}$, $R^{VII}$ and $R^{VIII}$ are each hydrogen or a hydrocarbyl group, provided that one of $R^V$ or $R^{VI}$ is hydrogen, one of $R^{VII}$ or $R^{VIII}$ is hydrogen, and at least one of $R^V$, $R^{VI}$, $R^{VII}$ and $R^{VIII}$ is a hydrocarbyl group; and wherein said copolymer has been functionalized by a method comprising:
    selectively hydrogenating said copolymer to provide a selectively hydrogenated copolymer;
    functionalizing said selectively hydrogenated copolymer to provide a functionalized copolymer having at least one polar functional group; and
    post treating the functionalized copolymer with a post-treating agent.

30. The dispersant modified fluid of claim 29, wherein the functionalized copolymer is modified, prior to post treating, by reaction with a Lewis base selected from the group consisting of a monoamine, polyamine, polyhydroxy compound, reactive polyether, or a combination thereof.

31. The dispersant-modified fluid of claim 29, wherein said dispersant substance is included in an amount of from about 0.001% wt. to about 20% wt.

32. The dispersant-modified fluid of claim 29, wherein said dispersant substance is included in an amount of from about 0.1% wt. to about 10% wt.

33. The dispersant-modified fluid claim 29, wherein said dispersant substance is included in an amount of from about 0.5% wt. to about 5% wt.

34. The dispersant-modified fluid claim 29, wherein said fluid is selected from the group consisting of motor oils, transmission fluids, hydraulic fluids, gear oils, aviation oils, greases, normally liquid fuels, and lubricants.

35. The dispersant-modified fluid claim 29, wherein said lubricant fluid further comprises at least one additive selected from the group consisting of antioxidants, pour point depressants, detergents, dispersants, friction modifiers, anti-wear agents, anti-foam agents, corrosion and rust inhibitors, and viscosity index improvers.

* * * * *